US012053293B2

(12) United States Patent
Sorgini et al.

(10) Patent No.: US 12,053,293 B2
(45) Date of Patent: Aug. 6, 2024

(54) MICROSENSOR-BASED BREASTFEEDING VOLUME MEASUREMENT DEVICE

(71) Applicant: Coroflo Limited, Dublin (IE)

(72) Inventors: Francesca Sorgini, Dublin (IE); James Travers, Dublin (IE); Giuseppe Tussiwand, Curreggio (IT)

(73) Assignee: Coroflo Limited, Dublin (IE)

( * ) Notice: Subject to any disclaimer, the term of this patent is extended or adjusted under 35 U.S.C. 154(b) by 864 days.

(21) Appl. No.: 17/263,758

(22) PCT Filed: Jul. 18, 2019

(86) PCT No.: PCT/EP2019/069343
§ 371 (c)(1),
(2) Date: Jan. 27, 2021

(87) PCT Pub. No.: WO2020/025337
PCT Pub. Date: Feb. 6, 2020

(65) Prior Publication Data
US 2021/0169398 A1    Jun. 10, 2021

(30) Foreign Application Priority Data

Aug. 2, 2018 (GB) ...................................... 1812588

(51) Int. Cl.
*A61B 5/00* (2006.01)
*A61J 13/00* (2006.01)

(52) U.S. Cl.
CPC .......... *A61B 5/4288* (2013.01); *A61B 5/4312* (2013.01); *A61B 5/742* (2013.01);
(Continued)

(58) Field of Classification Search
CPC ..... A61B 5/4288; A61B 5/4312; A61B 5/742; A61B 2562/0271; A61J 13/00;
(Continued)

(56) References Cited

U.S. PATENT DOCUMENTS 7,607,965 B1    10/2009 Frazier
7,887,507 B2    2/2011 Tulsa
(Continued)

FOREIGN PATENT DOCUMENTS

GB    2552194    1/2018
JP    0788112    4/1995
(Continued)

OTHER PUBLICATIONS

P.C. Stainback et al., "Review of Hot-Wire Anemometry and the Range of their Applicability for Various Flows," Electronic Journal of Fluids Engineering, Transactions of ASME, Jan. 1, 1993, pp. 1-54.
(Continued)

*Primary Examiner* — Robert J Utama
*Assistant Examiner* — Justin L Zamory
(74) *Attorney, Agent, or Firm* — Stephen T. Scherrer; Monique A. Morneault; Scherrer Patent & Trademark Law, P.C.

(57) ABSTRACT

A nipple-shield mounted sensor with associated electronic interface and interconnect for measurement and display of milk flow and volume during breastfeeding. The sensor is mounted in the tip of the nipple-shield in order to minimise intrusion between mother and child. The sensor can be mounted transverse or parallel to the milk flow in the channel depending on the selected sensing technology. The dimensions of the sensor and associated cabling are such that the device does not appear substantially different to a nipple-shield alone, thereby having minimal impact on the feeding session. Microlitre flow levels are measured directly by the sensor in order to relay accurate, real-time information on milk volume back to the feeding mother. The electronics unit amplifies the sensor input and digitally processes the data with software algorithms to determine the (Continued)

fluid volume, and can be directly integrated in the shield or can constitute an external module depending on the nature of the sensing technology integrated in the flow channel.

24 Claims, 21 Drawing Sheets

(52) U.S. Cl.
CPC ....... *A61J 13/00* (2013.01); *A61B 2562/0271* (2013.01); *A61J 2200/76* (2013.01)

(58) Field of Classification Search
CPC ...... A61J 2200/76; A61M 1/06; A61M 1/062; A61M 1/064; A61M 1/066; A61M 1/0693; A61M 1/067; A61M 1/0697; A61M 1/06935; A61M 2205/3334; A61M 2205/3327; A61M 2205/3344; A61M 2209/088
See application file for complete search history.

(56) References Cited

U.S. PATENT DOCUMENTS

| | | |
|---|---|---|
| 7,896,835 B2 | 3/2011 | Dahan et al. |
| 8,280,493 B2 | 10/2012 | Kolberg et al. |
| 8,413,502 B2 | 4/2013 | Zemel et al. |
| 8,521,272 B2 | 8/2013 | Kapon et al. |
| 2008/0167579 A1 | 7/2008 | Ezra et al. |
| 2008/0264180 A1 | 10/2008 | Gakhar et al. |
| 2010/0217148 A1 | 8/2010 | Binder |
| 2013/0073211 A1 | 2/2013 | Hershkovich |
| 2013/0096461 A1* | 4/2013 | Sella .................... A61B 5/6823 600/573 |
| 2015/0223755 A1 | 8/2015 | Abir |
| 2016/0235353 A1 | 8/2016 | Nakar et al. |
| 2019/0250020 A1* | 8/2019 | Travers .................. A61J 13/00 |

FOREIGN PATENT DOCUMENTS

| | | |
|---|---|---|
| JP | 4634402 | 2/2011 |
| WO | 2011117859 | 9/2011 |
| WO | 2014087343 | 6/2014 |
| WO | 2018011225 | 1/2018 |

OTHER PUBLICATIONS

Sharma Neha et al., "Design of switching power supply using PWM modulator & Delta-Sigma modulator," 2016 Conference on Advances in Signal Processing (CASP)< IEEE, Jun. 9, 2016, pp. 6-71.
ISR/WO from PCT/EP2019/069343.

* cited by examiner

MICROSENSOR-BASED BREASTFEEDING VOLUME MEASUREMENT DEVICE

FIELD OF THE INVENTION

The present invention relates to breastfeeding volume measurement device and in particular to a device that incorporates a sensor that operably provides a flow measurement indicative of a volume of breast milk being produced.

BACKGROUND

Among breastfeeding mothers there is a need for accurate measurement of milk volume delivered to a baby; in the absence of this information many mothers turn to supplementation or give up breastfeeding completely due to concerns over the baby's nourishment.

There is significant prior art in this field. Devices which have been invented or produced may be classified into three main groups:

1. Offline indirect. A measurement is derived without directly measuring flow or volume; the calculated volume is presented only after the feeding session has completed. The most significant method in this category is pre- and post-measurement of the baby's weight. This is the only method which seems to be currently endorsed by national health services, but studies have shown it to suffer from very poor accuracy levels.
2. Real-time indirect. Again, a proxy measurement is used to derive delivered milk volume. In this case, though, the measurement may be relayed to the mother in real-time. There are a number of patent disclosures and products in this field, mostly centring around measurement of the mother's breast milk volume. Methods employed involve, e.g. Doppler flow, skin-conductivity, physical volume, etc. One method not involving breast measurement relies on an acoustic signature of the baby's swallow in order to derive volume. These methods tend to be extremely complex and instances which have entered the market as a product have omitted accuracy information and generally been poorly received due to reported inaccuracies.
3. Real-time direct. This is where the milk flow is measured directly as it passes from mother to baby, with the corresponding volume information being presented in real-time to the mother. Typical embodiments comprise a breast cup with a sensor mounted in or beside a milk channel which then leads to an artificial teat. Many sensor types have been proposed such as piezoresistive force, thermal gradient, mechanical turbine/reciprocating piston devices. While these devices in some instances are likely more accurate than the previous types, they also suffer from the problem of separating the baby from the mother's breast. The physical bulk of the sensor, or the required channel length, in each case is such that this separation is necessary.

Relevant examples of devices for measuring milk volume during breastfeeding are mentioned in the following prior-art.

US patent No. 20080167579A1 to Ezra discloses a breastfeeding device consisting of a nipple shield in which a thermal dilution gauge is installed in the flow channel embedded in the shield.

U.S. Pat. No. 7,887,507B2 to Tulsa discloses a device for breastfeeding which includes a nipple shield in which a milk duct is fabricated, and which is equipped with a temperature gradient sensor in the milk duct or a mechanical flow meter, plus sensors for monitoring other parameters such as temperature, viscosity, fat content, and chemicals presence.

US patent No. 2013073211 (A1) to Hershkovich discloses a breastfeeding device consisting of a nipple shield equipped with a microcontroller-based breast milk flow meter, with on-board dielectric detector plate means and a piezo-resistive force sensor mean.

JP patent No. 463440262 to Kaizen discloses a breastfeeding device measuring the volume of milk from the breast during a feeding session by the volume of milk present in a transparent pipe. It does not comprise any flow sensor in the nipple shield nor in the milk pipe.

US patent No. 20130096461A1 to Sella discloses an apparatus and method to determine and monitor the flow rates and volume of fluids excreted or secreted by the body. The sensor means includes thermistors and measures the flow rate of the fluid passing through a channel calculating the difference in resistance of the two thermistors. Sella's device includes a thermal flow meter sensor.

U.S. Pat. No. 8,521,272B2 to Yeda Research and Development Co Ltd discloses a device for monitoring breastfeeding by capacitance measurement, determining variations in electric capacitance of the breast during breastfeeding, and correlating the electric capacitance variations to an amount of milk consumed by the infant via electrodes placed on the breast.

EP patent No. 2388026A1 to Tritsch-Olian discloses a device to assist breastfeeding, which is applied on the mothers' breast and in which a flowmeter can be embedded to measure the amount of milk taken by the child. It consists of a nipple shield to which a milk reservoir is attached and connected to a milk pump. It does not give a measurement of the flow of milk directly given to the infant by the mother's breast, and the presence of a flowmeter is not detailed, but described in a generic manner.

WO patent No. WO2014087343A1 to Momilk discloses a device which evaluates the amount of milk left in the breast by measuring the impedance of breast tissue with electrodes placed directly on the breast, or embedded in a case or brassiere. This patent describes a volumetric indirect measurement method.

US patent No. 20100217148A1 to Inolact discloses a device monitoring the amount of fluid from an organ, milk from human breast included. It consists of electrodes to be placed on the breast for a volumetric evaluation of the same. The patent also describes the possibility to add acoustic sensors for the detection of baby's gulps.

U.S. Pat. No. 8,280,493B2 to Mamsense discloses a device monitoring the amount of milk secreted by the breast during breastfeeding by means of ultrasonic Doppler-effect transmitter probes on the breast for a volumetric evaluation of the same. This patent describes a volumetric indirect measurement method.

US patent No. 20150223755A1 to Digisense describes a device to give an estimation of the quantity of milk taken from a baby by an indirect method. It details the use of a system to be applied on a diaper and which includes an optical sensor to calculate the amount of food taken by the baby.

U.S. Pat. No. 7,607,965B1 to Frazier describes a device consisting of a pipe and a nipple shield, which allows the milk to flow directly from a mother's breast to an artificial nipple that is placed in the infant's mouth for feeding purposes. The device is intended to allow mothers to feed their babies without using pumps and without exposing themselves during breastfeeding. This device introduces a mechanical separation of the baby from the breast, and does not involve any sensor for flow measurement.

JP patent No. JPH0788112A to Etsuno-Hirose Electric describes a device measuring the amount of milk ingested during breastfeeding which is equipped with a microphone detecting when the baby sucks the breast. A connected CPU counts instead the number of times of suction to determine the amount of milk ingested. Ultrasonic sensors can be added to detect a change in movement when the infant sucks milk. This does not consider a direct measurement of milk flow.

US patent No. 20160235353A1 to Momsense-Nakar describes again a device monitoring the amount of milk provided during breastfeeding by means of a microphone to be placed on the infant throat to detect swallowing, and ear plugs to be worn by the mother. The described technology provides an indirect measurement of the amount of milk taken by the baby US patent No. 20080264180A1 to Kimberly-Clark Worldwide Inc describes a device using an acoustic method to detect the amount of milk provided. It includes an audio sensor and a receiver to detect, discriminate and count the number of liquid swallows to determine the volume of fluid ingested.

U.S. Pat. No. 8,413,502B2 to Zemel describes a device for the measurement of infant feeding performance, which includes a body portion with an end for receiving the fluid from a reservoir, the other end connected to a feeding nipple, the cross-sectional area of the second end being larger than the one of the first end, and a conduit communicating with the first and second end in which is included a pressure sensor, the monitored pressure indicative of the fluid flow in the channel. The pressure sensor described in this application is based on the venturi-meter principle, since the flow will pass through a channel which first part has a narrower section respect to the ending part.

WO2011/117859 describes a lactation measurement device which uses first and second thermistors provided upstream and downstream relative to one another and with respect to a flow channel. The elements are mounted at the walls or side of the flow channel. One of the thermistors is heated above the expected temperature of the milk, the disclosure is to the use of a constant absolute temperature for the heated element, and the cooling effect of the milk gives a measurement which is indicative of milk volume Despite these known approaches that fall within the broad category of "Real-time direct" measurement there continues to be a need for a system and methodology that will allow a measurement of milk volume without requiring bulky physical sensors and associated electronics.

SUMMARY

These and other problems are addressed in accordance with the present teaching by a device comprising a flexible nipple shield adapted to operably conform in shape with a nipple, the shield defining a flow-channel through which a volume of milk will operably pass from the nipple to a feeding baby, the device further comprising a flow sensor provided within the flow-channel in the nipple shield and in contact with the milk flow.

In one arrangement, the flow sensor comprises a member mounted in the flow channel and perpendicular to the direction of the milk flow. Upon this member is mounted a thermally sensitive resistive element which may be heated above the ambient flow temperature either by its own power source, self-heating, or by an external source. The movement of liquid over the element will have the effect of cooling the element which measurably changes the resistance of the element to allow a flow value to be derived. This method may be implemented to hold the current, voltage, or temperature of the element constant in regimes which are commonly termed constant current anemometry, CCA, constant voltage anemometry, CVA, and constant temperature anemometry, CTA, respectively, the latter being the most commonly used. In each case the change in resistance, the required compensation for this change, or the element power is measured by an electrical circuit and converted by means of an algebraic transformation to a flow measurement.

In another arrangement, the flow sensor comprises two members mounted in the flow channel and perpendicular to the direction of the milk flow, both members having thermally sensitive resistive elements mounted or integrated therein. One member remains unheated and is thus capable of measuring ambient milk temperature, while the other is heated to a known temperature increase or delta above this ambient value. In accordance with this arrangement, which differs from the previous arrangement which used absolute temperature measurements, this technique uses a known temperature delta between the two sensors, thereby allowing accurate flow measurement in the presence of varying ambient flow temperature.

In another arrangement, the flow sensor comprises two members mounted horizontally in the flow channel and parallel to the direction of the milk flow, the flow channel including a restriction with a larger section close to the nipple and a smaller section close to the baby's mouth, the first member of the sensor being placed in the larger section of the channel and the second member being placed in the smaller section. Each of the first and second members are configured to sense a pressure variation as induced by the fluid passing by each the members respectively, the pressure measurements as detected by each member then defining a differential pressure measurement which arises from Bernoulli's principle and provides an indication of the milk flow within the channel. This type of flow sensor is commonly referred to as a Venturi-meter.

In another arrangement, the flow sensor comprises one member mounted with an angle 'θ' respect to the flow channel and to the direction of the milk flow, the member emitting a frequency towards the flow, and the same member detecting the signal reflected by the milk flow, the shifted frequency arising from the Doppler effect providing an indication of the velocity of the milk within the channel. A range of frequency sources can be used such as ultrasound, visible-light, and infra-red.

In another arrangement, the flow sensor comprises a separate frequency source and a detector mounted with an angle 'θ' respect to the flow channel and to the direction of the milk flow, one member emitting a frequency towards the flow, and the other member detecting the signal reflected by the milk flow, the shifted frequency providing an indication of the velocity of the milk as the previous method.

In another arrangement, the flow sensor comprises two members mounted horizontally in the flow channel and parallel to the direction of the milk flow, the first member emitting an electromagnetic or mechanical frequency towards the flow, the second member placed after the first in the direction of the flow and detecting the signal reflected by the opposite wall of the channel, the shifted phase of the signal arising from the time of flight through the milk flow and providing an indication of the velocity of the milk within the channel. In this arrangement, each member may also act as both emitter and detector to provide time-of-flight information in both the forward and reverse flow directions thus allowing for more accurate flow resolution.

In another arrangement, the flow sensor comprises two couples of members with a know separation distance in the flow direction, mounted on the opposite sides of the flow channel, the couple of members on one side emitting an optical signal towards the flow and the couple of members on the opposite side detecting the optical signal. For each couple, the signal is interrupted or perturbed due to the passage of particles, bubbles or other means in the fluid stream, the time of flight of which provides an indication of the velocity of the milk within the channel.

In another arrangement, the flow sensor comprises two members mounted on the opposite sides respect to the flow channel and to the direction of the milk flow, the first member emitting an electromagnetic or mechanical frequency towards the flow, the second member placed after the first in the direction of the flow and detecting the signal propagated by the milk flow, the time of flight between the two signals providing an indication of the velocity of the milk within the channel. In this arrangement, each member may also act as both emitter and detector to provide time-of-flight information in both the forward and reverse flow directions thus allowing for more accurate flow resolution.

In another arrangement, the flow sensor comprises one or more couples of members mounted transverse to the flow channel and to the direction of the milk flow, the first member of each couple emitting a sonic or ultrasound signal towards the flow, the second member placed in front of the first member transverse to the flow channel and detecting the signal with a phase shift due to the time of flight through the milk flow, the shift of the detected ultrasound signal providing an indication of the velocity of the milk flow within the channel. In the case where more than one sensor couple is used, the combined signals may be resolved into a spatial cross-sectional image from which point flow and overall flow may be derived. This field is broadly referred to as tomography.

In another arrangement, the flow sensor comprises one member shaped with a high camber wing or hydrofoil profile mounted in the flow channel and respect to the direction of milk flow, the member anchored in the flow channel by means of a pivot placed at the trailing edge of the member, and kept in position via two flexible elements placed above and under the member, the flow rate being measured by the difference of elongation of the two flexible members respect to the resting condition, and sensed by strain gages on said members.

In accordance with the present teaching, such a device provides a real-time direct measurement of the milk volume being delivered to the baby while at the same time addresses separation issue problems associated with the prior art by minimising the physical size and flow-channel length of the sensor.

Accordingly, there is provided a device as detailed in the claims that follow.

DETAILED DESCRIPTION OF THE DRAWINGS

Figure 1:
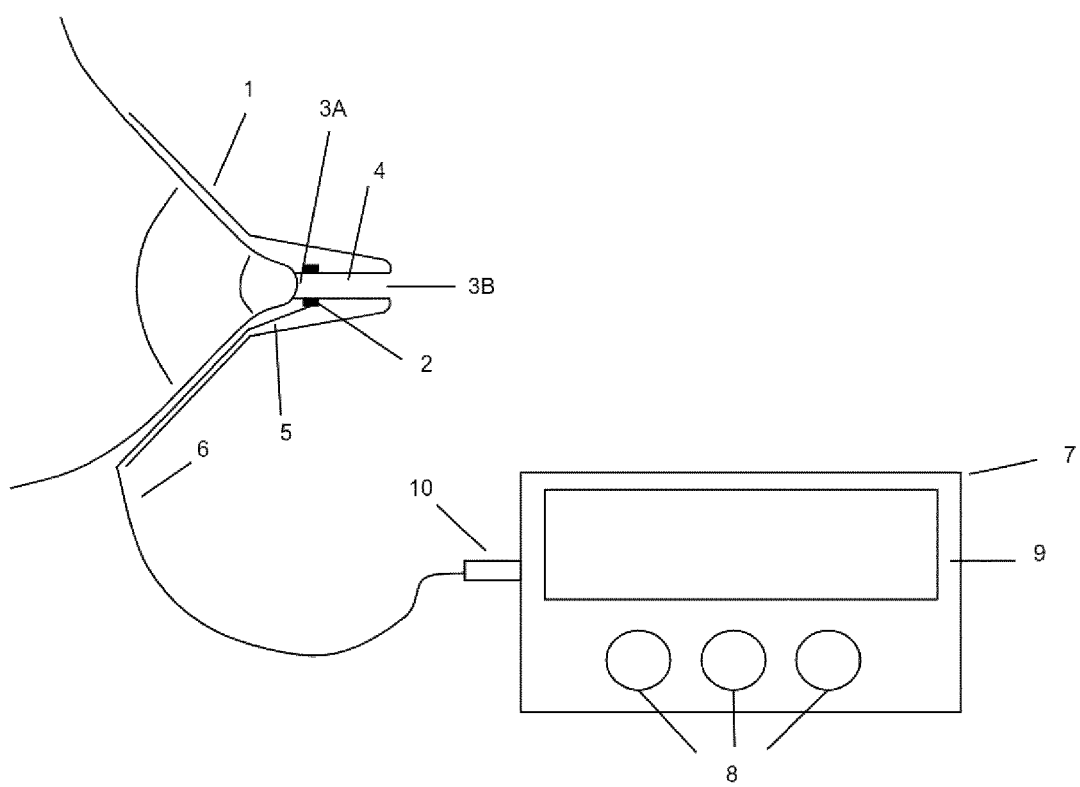
FIG. 1 is a schematic representation of a device in accordance with the present teaching located on a breast and coupled a measurement system.

Referring to FIG. 1 there is provided a device comprising a nipple shield/nipple guard (1) made of silicone rubber, TPE, or similar elastomeric material. It will be appreciated that the nature of this material imparts flexibility into the shield and will operably conform to the shape of a woman's nipple. A flow channel (4) is defined in the shield and extends through the shield. The flow channel has a nipple proximal end which, in use, is adjacent to the nipple when the shield is located on the breast. The flow channel further has a nipple distal end which, in use, is presented to the baby's mouth when the shield is located on the breast The device further comprises a sensor module (2) which is located in the flow channel (4) defined in the shield. To facilitate the placement of the sensor module in the channel, the sensor can be manufactured on a plastic (or other food-contact safe material) support and can be integrated in the polymeric shield (1) during the moulding process by gluing, or other clamping means. In another arrangement, it can be integrated in the shield (1) after the moulding process by means of adhesives (or other clamping means). The flow channel comprises an input port (3A) which is located at the nipple proximal end and an output port (3B) located at the nipple distal end of the flow channel (4), the flow channel providing a fluid communication path between the two.

The sensor module is placed within the flow channel so as to extend, depending on the selected embodiment, transverse or parallel to direction of flow of the milk from the input port (3A) to the output port (3B). In some embodiments of the present teaching, the sensor module is orientated with a defined angle 'ϑ' respect to the flow channel and in a fixed position respect to the milk flow from the input port (3A) to the output port (3B). The input port (3A) is in communication with, and typically in intimate contact with, the nipple and, in a breastfeeding situation, receives milk which is delivered into the flow channel and passes by the sensor module (2) prior to exiting from the outlet port (3B).

The milk passes the sensor module and is delivered through the channel (4) to the output port (3B) which is in communication with the baby's mouth so as facilitate the delivery of the milk from the mother to the baby. The suckling motion of the baby is communicated via the flexible nature of the nipple shield to effect an induced flow of milk through the flow channel.

The sensor module (2) desirably comprises a temperature sensor or a frequency shift detector respectively mounted transverse, or oriented with a defined angle 'ϑ' with respect to the fluid flow, and in a fixed position respect to the flow channel. The present teaching uses the change in resistance of a conducting element as it varies due to a change in temperature, or to a delay or frequency shift of a testing signal sent in the flow and related to the flow entity. The sensor output will provide an accurate measure of the induced temperature variation or of the frequency shift on the sensing element, which can be directly attributed to the flow past the sensor and hence a measure of the milk volume traversing through the device.

The sensor module can also comprise a mechanical element shaped with a high camber wing profile, mounted parallel to the flow and fixed into the flow channel via two flexible elements, on which strain gages can be mounted. The wing-shaped element can be fixed horizontally or vertically in the channel, depending on the application needs. In such a configuration, the present teaching uses the amount of deflection of said flexible elements, caused by the flow in the channel and sensed by strain gages, as a measure of the flow entity.

Electrical signals from the sensor are communicated from the shield. Such communication may be effected using for example a flat-flexible-cable (FFC) (5) which can be embedded in the material of the shield. By using a flat profile cable which can be embedded in the material of the shield, the profile of the shield can be minimised. The flexible cable can be specifically designed with a shape which ensures its flexibility and its integration within the thin polymeric layer of the shield (1). The cable then connects to a processing unit, which can be directly integrated in the lower part of the shield as already described in our PCT Application No. PCT/EP2017/067445 of 11$^{th}$ Jul. 2017. In another arrangement the processing unit may be provided as a standalone external processing unit (7). In such a configuration, the sensor will continue to be co-located with the shield. Where the processing unit is separate to the shield, the cable (5) desirably emerges radially from the shield at a lower position on the breast and connects to a processing module or processing unit (7) via an extension to the flat cable or a connection to a round cable (6), as exemplified with reference to FIG. 1. The processing module will typically incorporate a user interface comprising buttons (8) or similar type of user interface elements and a display (9) which may be LCD, LED, or other appropriate types.

To facilitate a decoupling of the nipple shield and as the processing unit, there may be provided, between the sensor and the processing module, a connector attached to the shield cable (10). The physical location of such a connector may well vary dependent on design constraints.

The operation of the processing module (7) and the possibility of integration of a memory device on the shield for storing data, which can include the use of a transmitter or transmitter/receiver arrangement to facilitate wireless communication between the sensor module and the processing unit/module, have already been described in our previous application (PCT/EP2017/067445 of 11$^{th}$ Jul. 2017) and apply also to the present teaching.

The processing module includes suitable electronic hardware and/or software that provides for amplification of the signal, digitisation and algorithmic processing to allow for an accurate display of milk volume to be presented to the mother in real time. In certain aspects the functionality of the processing unit may be provided by a smartphone, i.e. a mobile telecommunication device that performs many of the functions of a computer, typically having a touchscreen interface, Internet access, and an operating system capable of running downloaded applications or apps. By providing a software application or app that can be downloaded and then executed on the smartphone, the processing functionality to allow for an accurate display of milk volume to be presented to the mother in real time can be effected using the hardware already present on the smartphone. In this way, where the term processing unit is herein described it will be appreciated that this can be considered a smartphone executing dedicated software that is provided separately to the phone. The executable app will typically be provided through separate trade channels to the actual nipple shield—for example it will be accessed through an iOS or Android app store, as will be appreciated by those of ordinary skill.

This may incorporate further electronics such as a memory device for storing sensor calibration as well as historical feeding records. In this way a shield may include dedicated electronics and/or memory that will facilitate a personalisation of a specific shield. It will be appreciated that accuracy of the measurement may require calibration and by having a memory associated with each device it is possible to uniquely provide and store individual calibration routines for specific devices. Such a memory could also be used to store historical logged data indicative of actual measurements take using the sensor. This could allow use of the device separate to the processing unit. On a re-coupling of the connector to the processing unit (7) measurements that were taken during the "offline" period could be relayed to the processing unit (7) and the information displayed to the user.

Per the present teaching, by incorporating a memory on the shield side of the system as opposed to relying on a memory incorporated solely in the processing unit, the present teaching facilitates a record storage on the shield itself. As detailed above, this facilitates a personalisation of the shield, while the processing module may be generic in nature allowing for connection to multiple sensors provided on different shields. Further to this a data-logging module may be provided which has the capability of reading off and collating feed information against personal or other data for recording in e.g. a maternity hospital situation.

Such a memory unit could be provided as a physically separate unit to the shield but in electronic communication with the shield. Such communication could be provided by a physical cabling—such as shown with respect to the coupling of the processing unit to the shield. In such an arrangement the requirement to provide additional memory storage on the shield—with its associated bulk—can be minimised and yet the facility to provide a personalised storage for a specific shield can be provided.

It will be appreciated that such a memory element may be used for storing calibration coefficients of the flow sensor. Other uses would include storage of historical feeding data or sensor wear and/or use information. In this latter application, the device could be configured to provide a visual indicator of actual usage and then provide the user with information regarding possible need to change the sensor module. The sensor module could be provided as a removable or replaceable component and could for example be provided as a component of a feeding brassiere. Such a brassiere could be arranged to receive a first and second sensor module which provide an indication of milk volumes generated in each of a left and right breast respectively. In this way, the volume of milk from each breast can be individually detected and tracked for data logging and review purposes.

In certain arrangements the sensor module is coupled directly to the processing unit using a direct cable extending from the nipple shield. To allow flexibility and avoid the need to always be physically connected to the processing unit, the cable could have embedded therein or have coupled thereto the memory element which advantageously allows for storage of data during periods of non-connection to the processing unit. This would facilitate use of the sensor module without requiring physical connection to the processing and provides a more portable sensor arrangement.

Other configurations that could be employed to avoid direct physical coupling at all times include the use of a transmitter or transmitter/receiver arrangement to facilitate wireless communication between the sensor module and the processing unit. This transmission could use any one of a number of protocols such as for example at least one of WiFi™, Bluetooth™ or ZigBee™ protocols to communicate with a remote device.

In this way it will be appreciated that an overall measurement system provided in accordance with the present teaching includes a processing unit and a separate sensor module, the processing unit configured to receive flow sensor data from the sensor module and provide a visual indication of the flow measured. The processing unit may desirably incorporate a data-logger configured to collate received flow sensor data with at least one of personal information, time-of-day, medical notes. The actual physical form of the processing unit may vary. For example, the processing unit may be integrated into a wrist unit to be worn during feeding.

The actual processing of the data recorded may include storage of historical feeding records for subsequent retrieval and display in a numeric or graphical fashion. This may allow individual election of a measurement from one of a left or right breast to facilitate independent tracking of milk flow from each breast independently. A visual display may provide a graphical representation of pulsations of milk flow such as in the form of a bar-graph, a dial, or the appropriate percentage of the display becoming inverse in response to a dynamic reading sensed. Such a data processing may be configured to provide real-time accuracy bounds of a given measurement in a numeric or graphical fashion and could be arranged to track usage of the device and provide an indication of when actual usage approaches pre-calibrated expected usage.

The construction of the sensor module may resemble that of the schematic representations shown in FIG. 2A-D. The sensing module can be fixed within the flow channel in the shield using appropriate adhesive or mechanical clamping means.

Figure 2A:
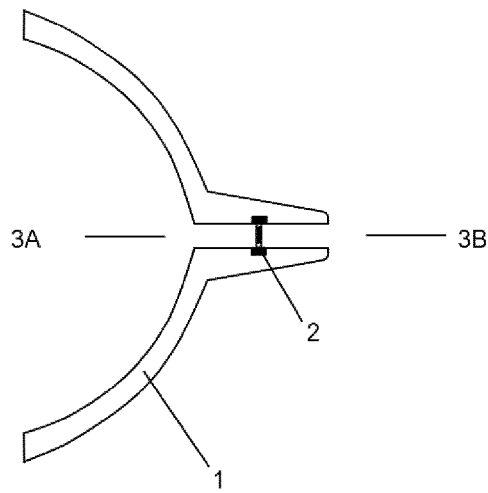
FIG. 2A is a schematic detail, in section view, of the device of FIG. 1, in accordance with an embodiment of the invention using a single-element anemometer.
Figure 2B:
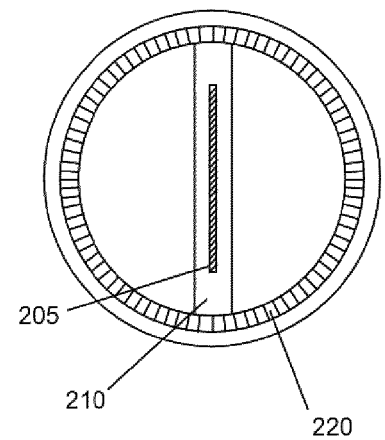
FIG. 2B is a schematic detail, in front view, of the device of FIG. 2A.

FIGS. 2A and 2B show an exemplary arrangement, in section and plan view, where the sensor module (2) is embodied in a single active element (205) and is placed between the input port (3A) and the output port (3B) of the flow channel, and perpendicular to the flow. The active element (205) of the sensor module can be mounted on a supporting substrate (210), said substrate located at the level of the flow channel cross section by means of a supporting ring (220) made of metal or other food-safe material. The active element (205) is desirably a heatable resistor, whose resistance is dependent on the temperature of the resistor. The heatable resistor is, as shown in the schematic of FIG. 2B, preferentially located within a mid-portion of the flow channel. This has been identified by the present inventors as a particularly advantageous location as the sensed flow is least affected by any boundary effects or turbulence that would be experienced if the resistor was located at the edge or sides of the flow channel. The effects of any fouling of the resistor are also minimised by its location away from the side walls. The frequency response of the sensor is also improved as the supporting substrate (210) is in more intimate contact with the measured fluid than would be possible by having it mounted or otherwise located at the side of the channels. The flow that passes by the resistor within the mid-portion of the channel can be considered more likely to be laminar flow, and is not compromised by the surface effects of the side walls that can, with fouling, exacerbate any turbulent or fouling effects on the fluid flow.

By operably heating the resistor to a first temperature, $T_1$, which is greater than an ambient temperature, $T_2$, of milk flowing in the flow channel, when the resistor is exposed to a flow of milk passing through the flow channel it will experience a measurable cooling effect. This ambient temperature is desirably measured from a second temperature sensor that does not have to be located within the mid portion of the flow channel. This second temperature sensor could, for example, be located within the body of the nipple shield or within the channel wall itself. The second temperature is configured to provide an output which is indicative of the actual temperature of the milk flowing within the channel. This indicative actual temperature is more constant over time, it does not need to measure signals having a frequency component greater than about 1 Hz and hence this second sensor can be located out of the flow. In contrast, the first operably heated resistor will provide an output that is rapidly fluctuating over time, the frequency components of the flow signal are typically up to around 100 Hz, and hence is provided within the actual flow path.

The sensor module is configured to use the measurable cooling effect to generate an output signal indicative of the milk flow within the channel, and hence the volume of milk that is ultimately consumed during any one feeding session.

The electrical circuitry that is used to sense this temperature effect on the resistance characteristics of the resistor can be generically termed an anemometry circuit, the anemometry circuit being coupled to the resistor and arranged to monitor electrical characteristics of the resistor and to use changes in those monitored electrical characteristics to generate the output signal.

The anemometry circuit is desirably selected from one of a constant temperature anemometry (CTA) circuit, a constant current anemometry (CCA) circuit, or a constant voltage anemometry (CVA) circuit. It will be appreciated that these terms relate to three broad methods of electronic control of the anemometer element and can be distinguished as follows:

CTA: The resistance of the heated element is a measure of its temperature. By sensing this resistance through a bridge circuit or similar a feedback signal can be generated which modifies the excitation of the bridge in order to hold this value (and consequently the temperature) constant. Using this method, the feedback excitation voltage is the measurement quantity.

CCA: A constant current is applied across the heated element. As its resistance changes with temperature, the voltage across it changes correspondingly and this forms the measurement quantity.

CVA: A constant voltage is applied across the heated element. As its resistance changes with temperature, the current through it changes correspondingly and this forms the measurement quantity.

Figure 7:
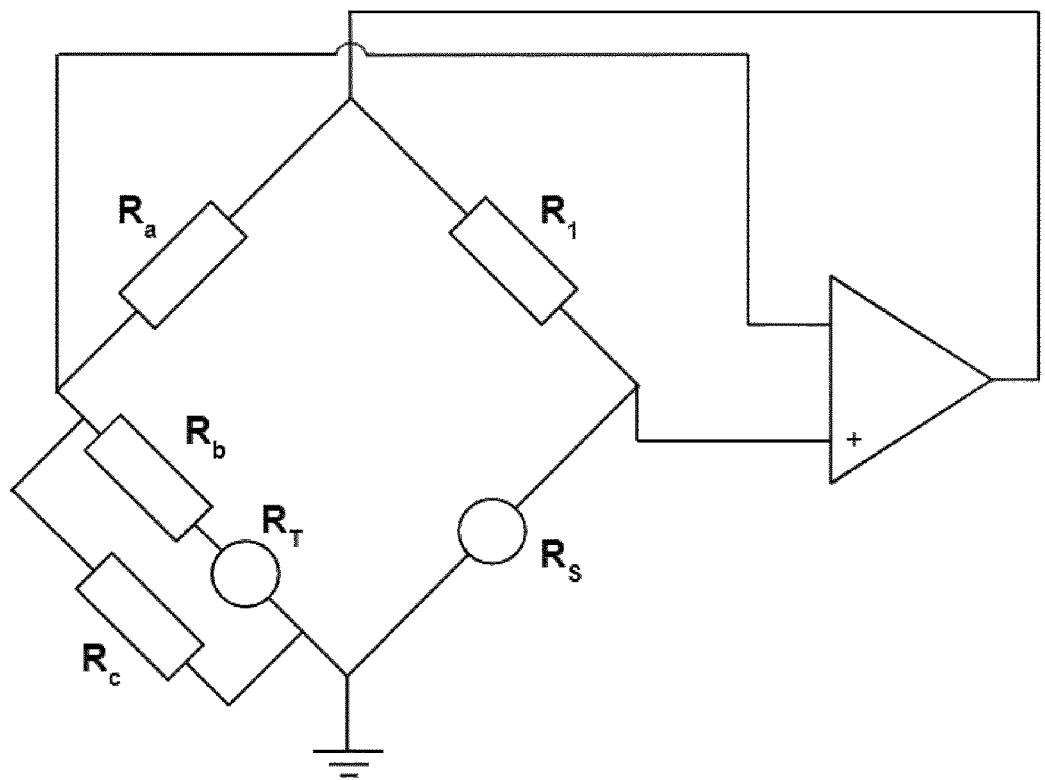
FIG. 7 is an example of a Wheatstone bridge circuit that can be advantageously used to control a CTA circuit in accordance with the present teaching.

The CCA and CVA methods do not require any feedback control of the sensor response, so may be implemented with simpler electronics. They do however allow the temperature of the sensing element to vary with flow thus allowing the thermal time constant of the sensor to negatively impact on the response time. Given the relatively low cost of more advanced electronics, the CTA method is preferable to choosing a smaller, more fragile and more expensive sensor element to compensate the difference in response from the control method. Control of such a CTA arrangement can be achieved for example through a Wheatstone bridge circuit feeding into a differential amplifier (a simplified arrangement is shown in FIG. 7). The output of the amplifier feeds a power stage which constantly updates the excitation of the bridge to keep it balanced. The excitation voltage forms the measurement quantity and can be read by an analog-to-digital converter (not shown).

In the exemplary arrangement of FIG. 7, resistor $R_s$ is the heated sensor with $R_1$ as its balance resistor. In a non-referenced implementation $R_a$ and $R_b$ would complete the bridge on the other arm, nominally providing balance between the two sides.

Where temperature compensation is also required, a temperature sensing ($R_t$) and compensation resistor ($R_c$) are added. These are intended to adjust the bridge reference in response to ambient temperature changes such that their effects are nulled and only flow response is measured.

There are a number of practical issues with this implementation especially in the context of a scalable consumer device:

While standard resistors may be specified to very tight tolerances, the variable resistors, $R_s$ and $R_t$, may have tolerance ranges up to ±20% or more. This can imbalance the bridge to the point that the amplifier or feedback is outside an operable range. The remedy to this is individual selection of the other resistors in the bridge to bring the circuit back into range. This means that each circuit needs to be uniquely provisioned which precludes high-volume manufacturing techniques.

Due to the above resistor-based and other variations in the electronics and sensor, the feedback circuit can suffer from stability issues potentially causing resonance in the output. The solution is either to tune the design for over-damped response thereby limiting the performance of the circuit or individually tuning each circuit adding significant manufacturing time.

The temperature compensation circuit has the further issue that the response curve of the temperature reference needs to exactly match that of the heated sensor in order to eliminate the temperature signal. This is difficult to achieve for most sensor types; for example thermistors will have different characteristic response (β-value) even within the same product family and this response also has a specified tolerance range which can alter the curve on a part-to-part basis. Errors due to mismatch here are built into the circuit and are difficult to compensate later in the signal-path.

The Wheatstone bridge resistors and the excitation power-stage all consume significant power. Typically, the circuit will be provided with a fixed voltage source and the excitation voltage is generated through a device such as a transistor which will appear as a resistive load. The heater may claim only a minority of the power budget, which for a battery-operated device is not ideal.

Figure 8:
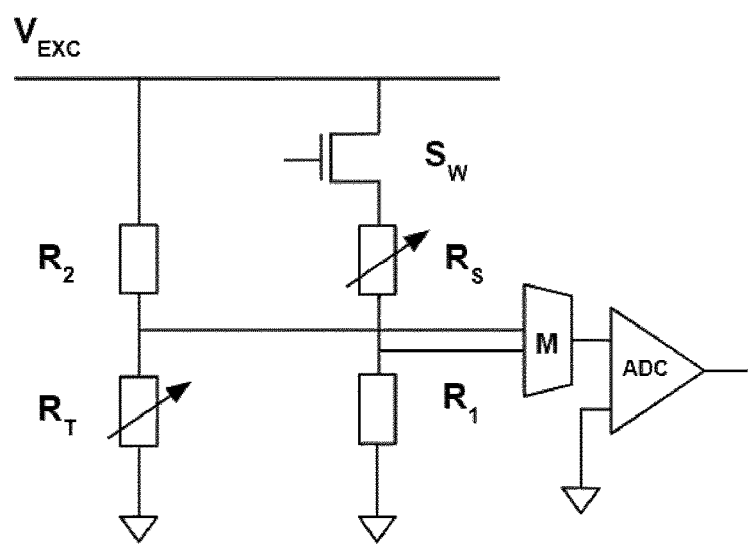
FIG. 8 is an example of a digital pulse circuit configured to apply a fixed voltage over a measured time window to a heater circuit.

The alternative to this is a digital pulsed method where a fixed voltage is applied over a measured time window to the heater circuit, an example of the type of circuit that can be usefully employed being shown in FIG. 8. In this configuration the heated resistor ($R_s$) and the temperature reference ($R_t$) are in separate resistor divider arrangements completed with $R_1$ and $R_2$. The reference arm is permanently connected to the excitation voltage $V_{exc}$, while the heater is selectively connected to it via a switch ($S_w$). The output of both dividers is fed into a multiplexer (M) which selects one or other signal to feed to a single-ended ADC for conversion. The advantages here are as follows:

The signals from the resistor circuits are now analysed in the digital domain and feedback is generated through digital control of the switch device. This eliminates the potential for instability as the digital control portion has a much higher bandwidth than the analog sensor circuits.

As the resistor circuits do not have any direct feedback, their range can be selected to match that of the ADC allowing for any tolerance variations. These variations may then be calibrated out in the digital domain, including variations in the response curve between the temperature and heated element.

The power requirements are much lower. Even though the resistor arrangement looks similar to the Wheatstone bridge, the values are very different as they do not need to balance each other. The ADC input can be referenced to a low value in the range 1 to 2V which means that only small signals need to be generated on the inputs. For the temperature sensor a high-valued resistor of e.g. 10 kΩ can be selected. Where $V_{exc}$ is in the range 10 to 20V this means a higher value of $R_2$ of the order of 100 s kΩ to generate an output in the ADC range. On the sense side the combined resistance is lower as it is intended for the heater to consume power. This power is concentrated in $R_s$ and again $R_1$ is only large enough to generate a voltage in the ADC range. Unlike the analog bridge the switch for the heater is turned fully on or off so only presents a very small resistive load. Using this configuration, it is possible for 90% or more of the power in the network to be consumed where it is required in the heater resistor.

Finally, the architecture above lends itself very well to currently available microcontroller (MCU) chips. These are readily available with the multiplexer and ADC circuits built in along with the digital processor and, in our case, the Bluetooth radio. This means that almost all of the functionality can be realised in a single low-cost device and all control and calibration aspects can be modified in firmware.

The anemometry circuit can be used with or without a temperature reference to measure fluid flow. Where no reference is available, the temperature difference or delta (ΔT) between the heated resistor temperature ($T_1$) and the ambient temperature ($T_2$) of milk flowing in the flow channel needs to be large relative to potential variations in ambient temperature to ensure accuracy. Large ΔT values in liquid anemometers can cause bubble formation which degrades sensitivity, so a referenced anemometer is the preferred option. The smaller ΔT also implies lower power which is critical for a battery-powered device. The ΔT value will desirably be maintained to 20° C. or lower.

Given the fact that breast milk temperature is related to body temperature of the feeding mother, typically the $T_2$ values are around 37° C. Heating the resistor to a value less than or equal to 50° C. will provide a sufficient variation or ΔT value to allow measurement. It will be appreciated that the localised heating of the resistor will have an insignificant effect on the overall temperature of milk flowing through the flow channel and hence the feeding baby will experience no discernible variation in temperature through the active heating of the resistor.

In this regard, it will be appreciated that the dimensions of the heatable resistor—or heated element—is an important consideration. The larger the element, the greater the thermal mass and slower the thermal response time. If the element is too small, however, durability becomes a factor, and fouling by particles in the liquid has a greater relative effect on sensor sensitivity. The typical sucking rate of an infant is in the region of 1 to 2 Hz and consequently, in order to detect the full range of flow transients, the sensor bandwidth should be in the range 10 to 200 Hz. The size of sensor which we have found to fall within this range for the sensor types considered is 0.3-0.6 mm length, with a preferred, but not limited to, spherical geometry. The range of the correspondent sensor surface area which will be in thermal contact with the milk is typically in the range 1-1.5 mm².

The sensing element will be advantageously positioned in the centre of the flow channel within the nipple shield. Said centered position will allow for the stability of the sensor inside the material of the shield, ensuring the resistance of the device to perturbations coming from the baby's mouth during the feeding, as well as from external objects which may be used during the device maintenance.

As described above, the heatable resistor or sensing element is desirably located within and ideally suspended within, the flow channel. The suspended arrangement of the sensor module will reduce the boundary effects of the flow channel walls on the temperature measurements. The active element (205) in this arrangement is heated and kept at a constant temperature by associated circuitry connected to it (not shown). During breastfeeding, the milk flow in the channel generates a decrease in temperature of the heated element, which corresponds to a variation in the value of the resistance of the same element which is detected by the connected measurement circuitry (not shown). The use of such circuitry for thermistors and the like is well known—for example in temperature measurement circuits that employ thermistors.

Figure 2C:
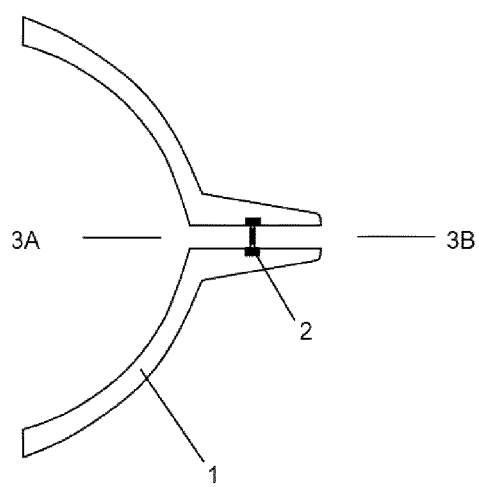
FIG. 2C is a schematic detail, in section view, of the device of FIG. 1, in accordance with an alternative embodiment of the invention where an anemometer with a separate temperature reference element is used.
Figure 2D:
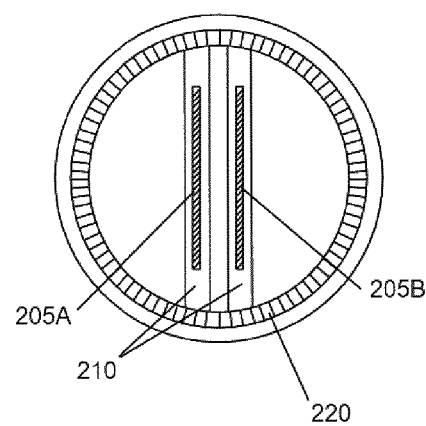
FIG. 2D is a schematic detail, in front view, of the device of FIG. 2C.

FIGS. 2C and 2D show another exemplary arrangement, in section and plan view, where the sensor module (2) is constituted of two active elements (205A, 205B) and is placed between the input port (3A) and the output port (3B) of the flow channel, and perpendicular to the flow. The active elements (205A, 205B) of the sensor module can be mounted on a supporting substrate (210), said substrate located at the level of the flow channel cross section by means of a supporting ring (220) made of metal or other food-safe material. Similarly, to that described above, the suspended arrangement of the sensor module will reduce the boundary effects of the flow channel walls on the temperature measurements. The first element (205A) is heated and kept at a constant temperature by the circuitry connected to it (not shown). A second sensing element (205B), placed close to the first heating element (205A), measures the temperature variation of the fluid respect to the temperature of the heated element by detecting the variation of the value of its resistance via the connected circuitry (not shown).

Given the very small flow measurements being taken, the temperature sensing elements of the sensor could advantageously be shielded or isolated from the effects of the temperature gradient of the air in conditions of absence of milk in the channel.

In a digital domain, in order to provide an active heating of the heated sensor (205), the present teaching requires a control method to feedback heater and temperature values to the switch control and maintain the heater at the desired ΔT. Two common approaches are Pulse-Width Modulation (PWM) and Delta Sigma (ΔΣ) modulation. Typically PWM describes the bit-pattern while ΔΣ modulation more often describes the overall feedback system; for the purpose of this application we will consider both in the context of the bit-pattern only.

Figure 9:
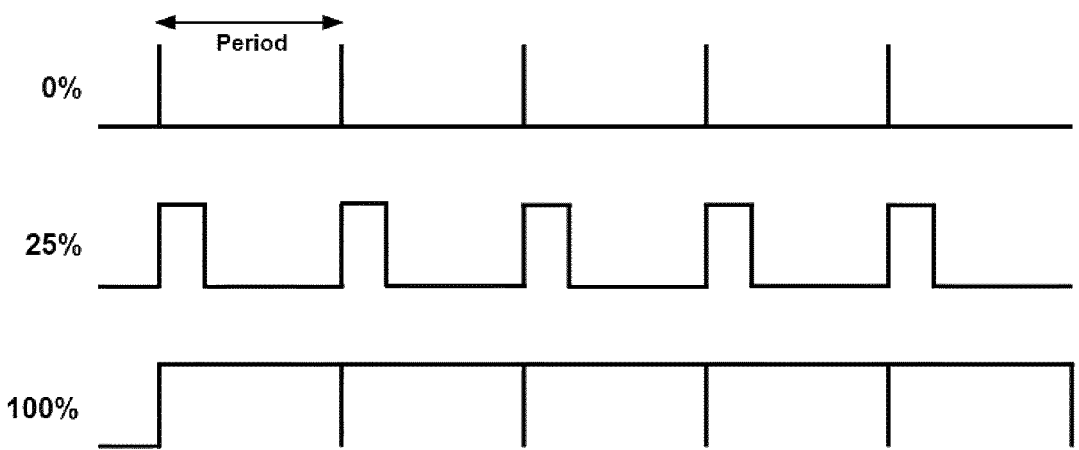
FIG. 9 shows a sample window for signals used in the context of a PWM circuit.

In the case of PWM a fixed sample window is selected over which the width of the on-pulse is modulated as shown in FIG. 9. In the case of the anemometer at the start of the period the switch would turn on to power the heater. The response of the heater would then be monitored (by an analog to digital converter, ADC) until it rises above the setpoint temperature through self-heating at which point the switch would be turned off until the end of the period. In this way the width of the pulse is a metric for how much power was required to bring the heater above the threshold for this period.

ΔΣ modulation is similar in that it uses a fixed period, but it differs in that for each period the switch will be continuously on or off based on the threshold value prevailing at the start of the period. An example output is shown in FIG. 10 for a sinusoidally varying input.

Figure 10:
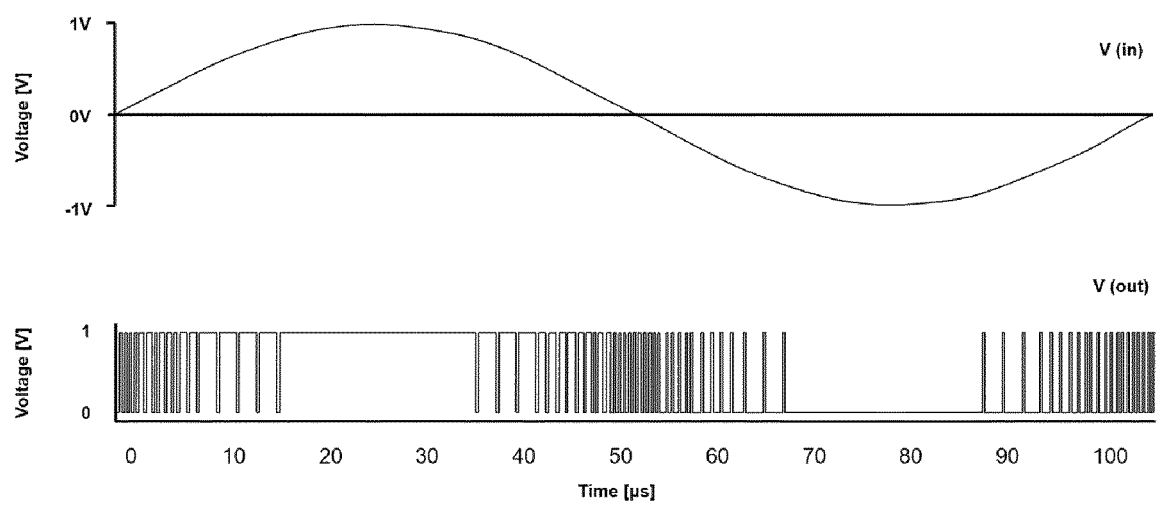
FIG. 10 is an example of the output from a $\Delta\Sigma$ modulation circuit.

It will be appreciated from the schematic of FIG. 10, that the longer high or low duration are not different period lengths, rather individual periods with the same value clumped together. The measurement value of power in this scheme is the number of pulses which are high during a given duration where the duration is an integer multiple of the period width. The ΔΣ pattern is algorithmically and computationally simpler to implement as it only requires one ADC sample and switching decision per period, while PWM requires constant sampling during the on-phase. In order to achieve the same resolution, however, ΔΣ requires a much smaller period/higher pulse frequency as it is the pulse count which is measured. In a switching scenario with real components such as MOSFETs this frequency has limits due to rise/fall times and switching power. For this reason within the context of the present teaching, the present inventors have realised that a PWM scheme is preferable: high ADC sampling rates and computational power are readily available whereas high-frequency switches can be difficult to implement and power hungry, along with presenting potential Electromagnetic Interference (EMI) issues.

A device per the present teaching is advantageously used without a mains power supply. The power components—the heatable resistor, etc.—require power for functionality and as such the device is typically provided with a dedicated power supply in the form of a battery. Desirably, the device includes a rechargeable (lithium-ion) battery, the capacity of which should not inconvenience the user with very frequent charging. Battery life between a couple of reasonable-duration (1-hour) feeds equivalent to 1 day of use and up to 1 week or more of use should be considered. The measured power requirement of the anemometer heater circuit is around 10 mW, while the digital system and Bluetooth power budget is around 5 mW. The nominal battery voltage of 3.7V is stepped up or down for the different systems as appropriate with the associated converter losses. In order to calculate average current for battery sizing (in mAh), we will assume all converters to be equivalent to a linear step-down to 3V with the associated power-loss of 0.7V drop-out.

$$I=P/V$$

$$5\text{ mA}=15\text{ mW}/3V$$

Where I: current; P: power, V: voltage. With an average current of 5 mA, the minimum battery capacity will need to be 10 mAh for 2 1-hour feeds. In order to accommodate 20-40 feeds allowing for a full week of use for some users, capacity of up to 200 mAh could be considered.

Figure 2E:
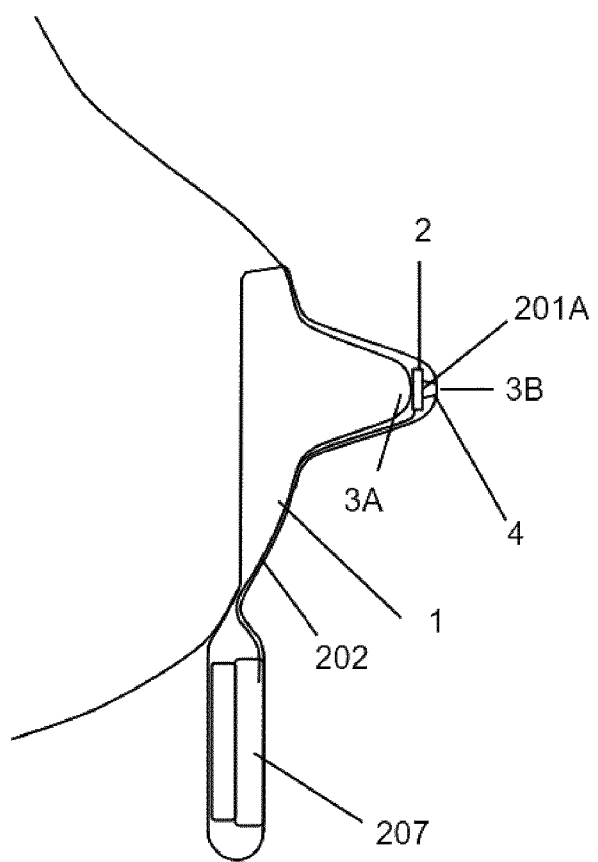
FIG. 2E is a schematic showing the device of FIG. 1 coupled to a processing unit.
Figure 2F:
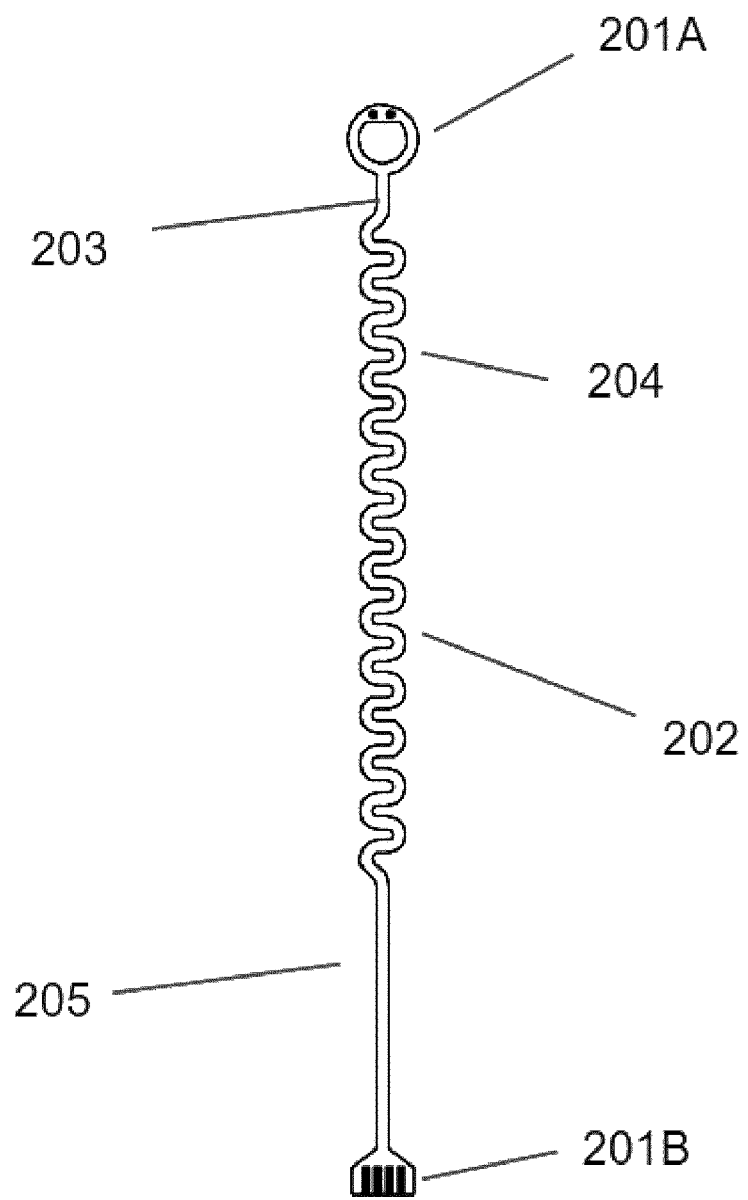
FIG. 2F is an example of a flexible cable that can be advantageously used in the context of the present teaching.

FIGS. 2E and 2F shows how device of FIG. 2A-2D can be coupled to a processing unit 207 via a flat flexible cable 202 that is integrated in the shield (1). The present inventors have realised that it is important that the shape of the cable will be particularly conformed to the shield profile to easily follow its movements during the device operation and handling. The selection of a proper configuration for the wire will be dictated by the necessity of a perfect mechanical match between the elongation capability of the flexible cable and the one of the polymeric shield. Especially when considering the entity of suction forces exerted by the baby on the nipple, a correct geometry for the cable will enable it to follow the elongation/deformation of the polymeric shield avoiding its breakage or detachment from the rubber. Furthermore, the particular geometry of the wire will ensure to reach a breakage point similar to the one of the polymeric shield for the selected rubber thickness.

In order to address the above mentioned points, the flat flexible cable will be designed as follows. The upper part of the cable will consist of a connector (201A) for the sensor module (2) placed in the flow channel. The flat flexible cable then continues with a linear pattern (203) extending from said connector (201A) for a length varying according to the selected dimensions of the shield, said linear pattern continuing in a wavy pattern (204), which becomes again a linear pattern (205) in the lower part of the shield, and ending in a connector (201B) to be inserted into the processing unit (207) in the lower part of the shield. The lengths of the wavy as well as the linear patterns will vary accordingly to the selected dimensions of the shield. The number and the configuration of the conductive patterns along the flat flexible wire, as well as those on the connectors (201A, 201B) will vary accordingly to the sensor module installed in the shield. By adopting a circuitous path, the cable has flexibility in multiple dimensions and can stretch in those dimensions without breaking. The snake-like pattern facilitates more applied tension than a linear path would.

The cable will be advantageously thin to fit into the shield profile (with a thickness in the order of 100 μm), and will be fabricated with a material (say, but not limited to, polyimide) which will ensure the flexibility of the substrate, and will allow the deposition of conductive patterns. It is important that the materials used for the fabrication of the flat flexible cable will ensure a low-noise connection, to allow for the transmission of small signals coming from the sensor module. Due to the sensitivity requirement to very low flow rates (upper μl/s to lower ml/s range) electrical amplification of the detected signals in the processing unit may be also required.

Figure 2G:
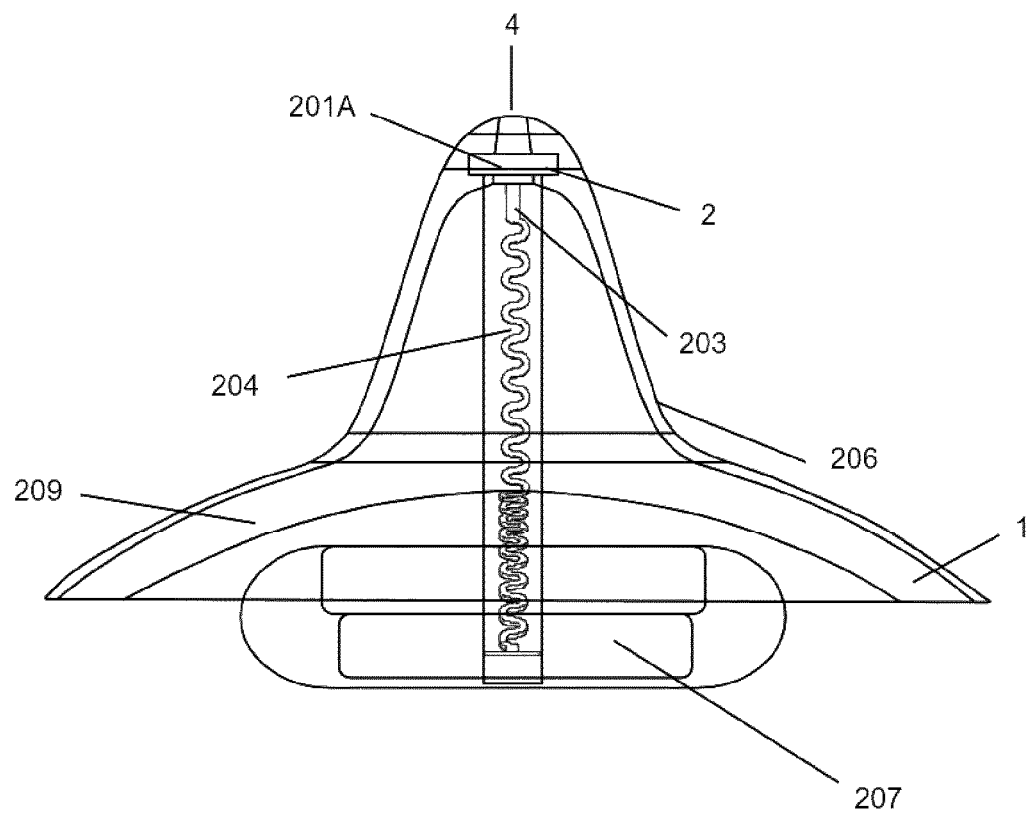
FIG. 2G is a schematic showing how the pattern of the flat flexible cable is designed to adapt into the geometry of the shield
Figure 2H:
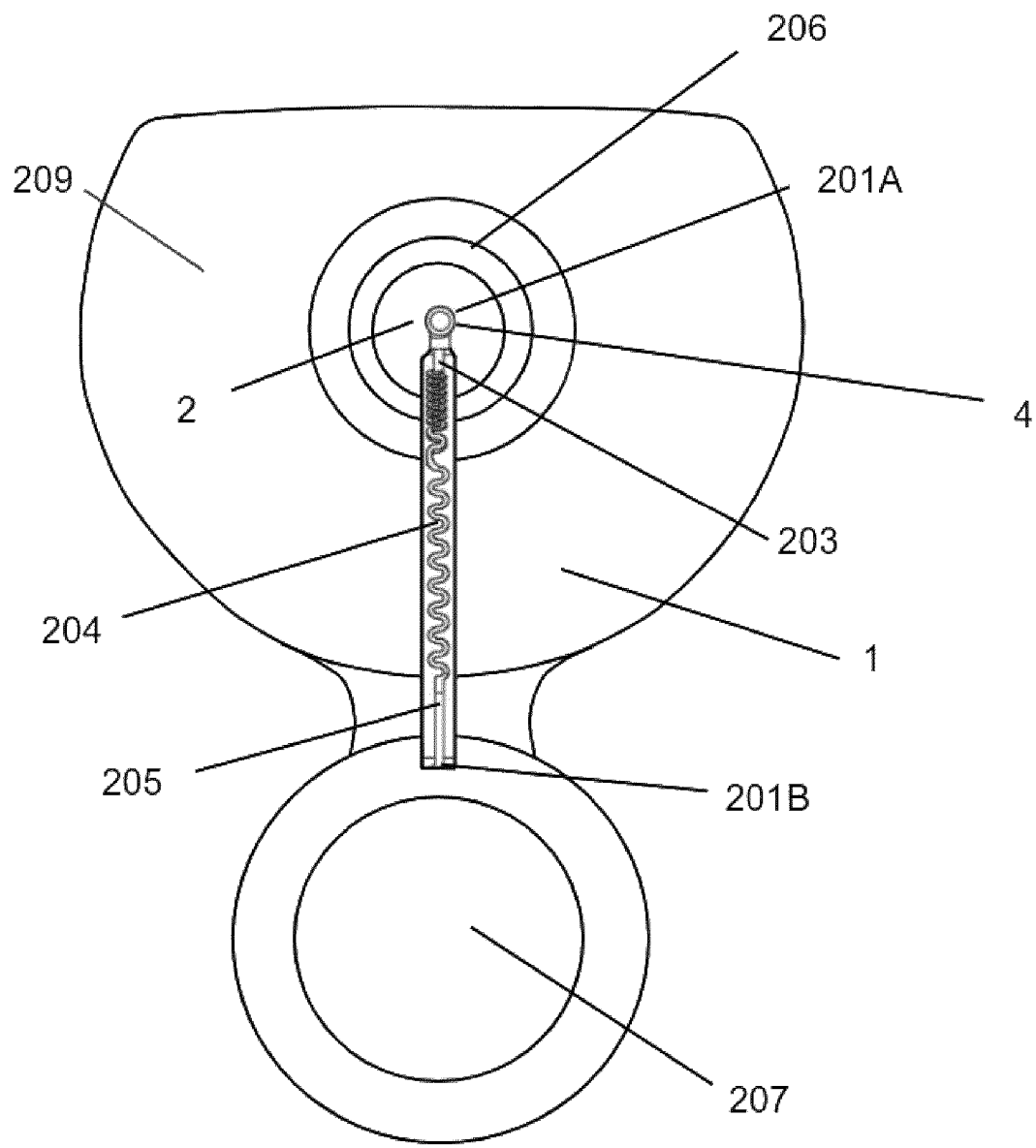
FIG. 2H shows in plan view how the flexible cable can connect between a sensor module and the connected processing unit.

The particular geometry designed for the flat flexible cable will facilitate its integration in the flexible shield, in a way that ensures the resistance and flexibility of the conductive pattern within the polymeric material of the shield. Referring to FIGS. 2G and 2H, the pattern of the flat flexible cable is designed to adapt into the geometry of the shield (1). The connector (201A) in the upper part of the flat flexible cable will be contacted in communication with the sensor module (2) within the flow channel (4), while the following straight part (203) of the cable will extend along the flow channel until reaching the conical part (206) of the shield which will be placed over the nipple. Said straight part of the cable will then bend at the junction between the flow channel (4) and the conical part (206) of the shield, and will continue with a wavy pattern (204). Said wavy pattern of the cable will extend radially along both the conical (206) and curved (209) parts of the shield, said curved part being instead placed on the breast, towards the embedded processing module (207) located in the lower part of the device. The flat flexible cable will become straight (205) again once reached the housing for the processing unit. The connector (201B) in the lower part of the flat flexible cable will be inserted into the processing unit in order to transmit the measured signal from the flow sensor (2) to the processing unit (207).

The integration of the sensor module, the processing unit and the flat flexible cable in the nipple shield will be obtained with a manufacturing method involving a two-steps injection moulding. Said manufacturing method will ensure an advantageous placing of the components into the flexible nipple shield.

Figure 3:
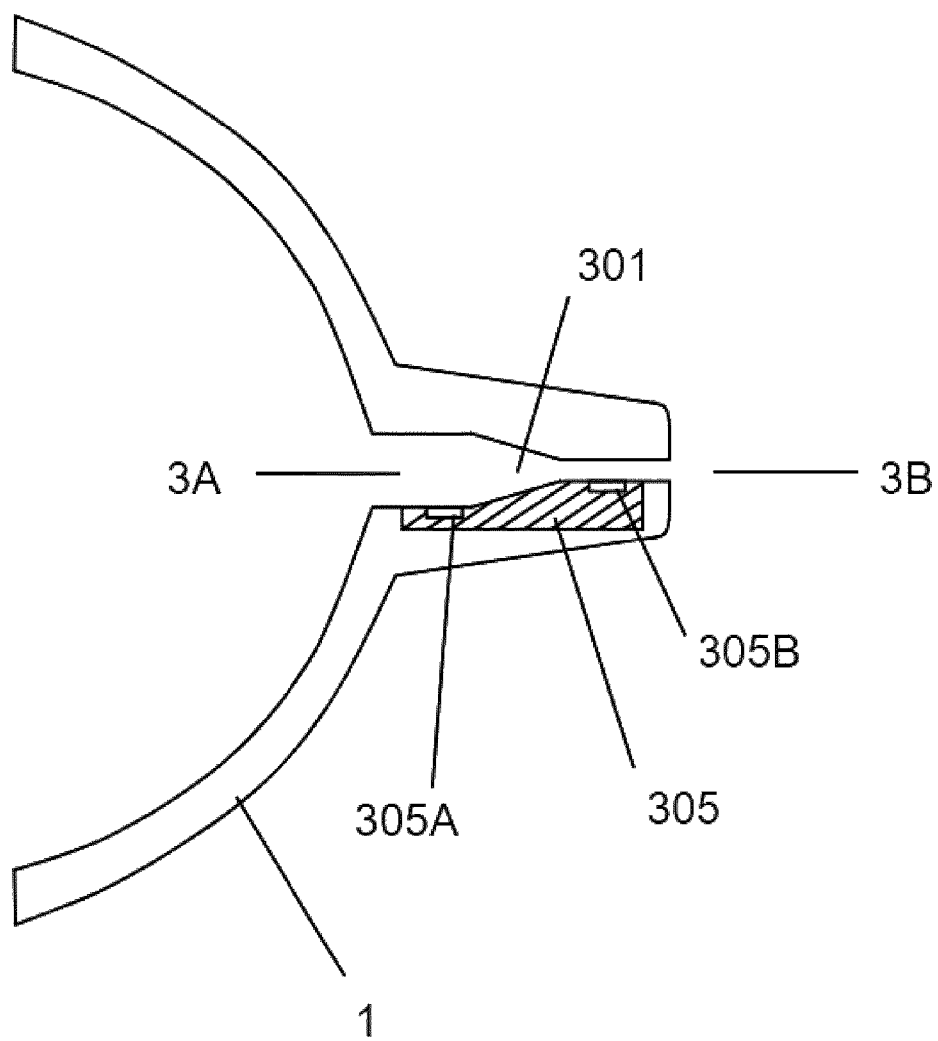
FIG. 3 is a schematic detail of the device of FIG. 1, in accordance with a further alternative embodiment of the invention using pressure sensors.

FIG. 3 shows another exemplary arrangement where the sensor module (305) is constituted of a differential pressure module placed in the flow channel in which a restriction (301) has been introduced. The sensing module includes a first pressure sensor (305A) close to the input port (3A) in the larger section of the flow channel, and a second pressure sensor (305B) close to the output port (3B) in the smaller section of the flow channel. The differential pressure calculated from the measurements of the two sensors via the connected circuitry (not shown) gives an indication of the milk flow in the channel.

Figure 4A:
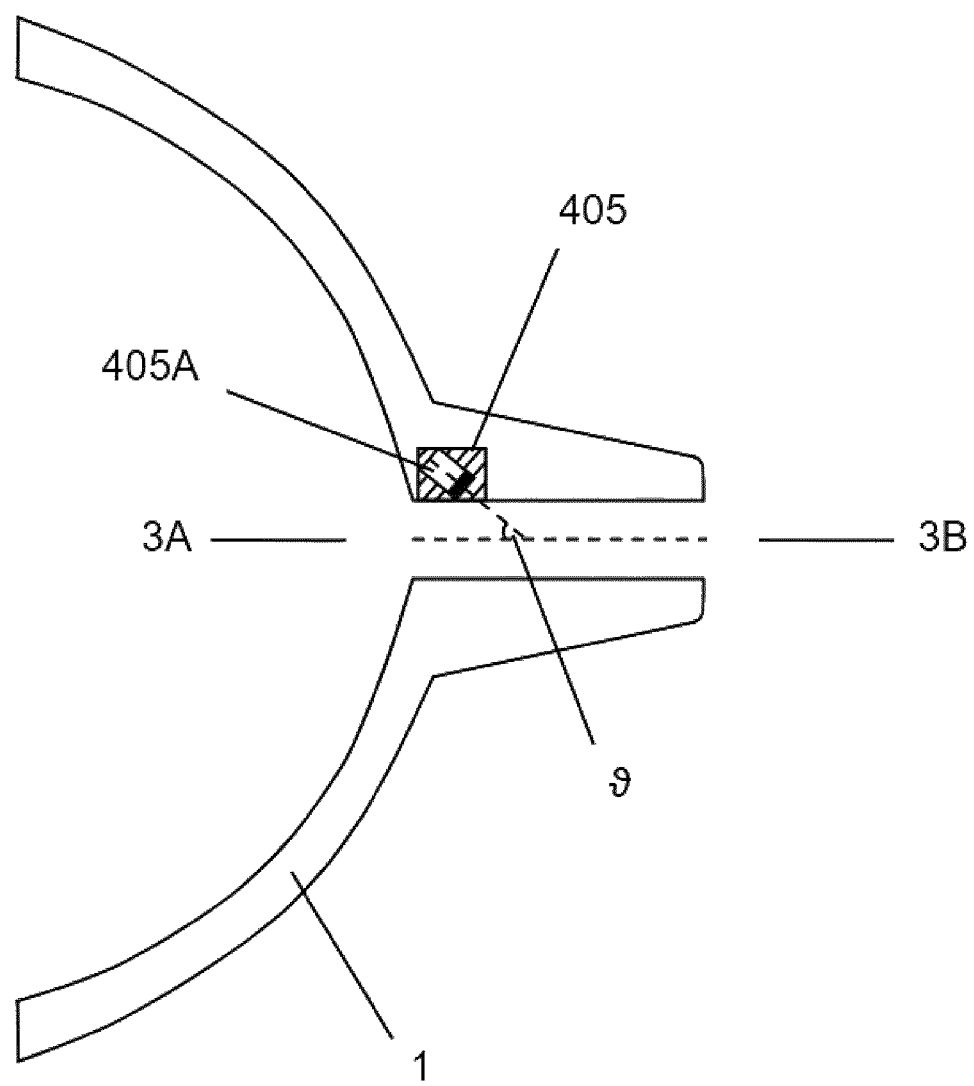
FIG. 4A is a schematic detail of the device of FIG. 1, in accordance with a further alternative embodiment of the invention using a single Doppler sensor.

FIG. 4A shows another exemplary arrangement where the sensor module (405) is constituted of one active element (405A) fixed in a stable position and oriented with a defined angle 'ϑ' respect to the flow channel and the milk flow. Said active element is close to the input port (3A) of the flow channel and serves as a frequency source, such as a light beam which can be used to illuminate the milk flow. The sensor module also includes a detector, which in this arrangement is co-located with the active element (405A) and is configured to receive the signal reflected by the fluid moving in the channel. Based on the Doppler effect, it is known that the velocity of the fluid is proportional to the frequency shift and with knowledge of the frequencies of both the emitted and detected light, processing circuitry can then make a determination of the actual velocity.

Figure 4B:
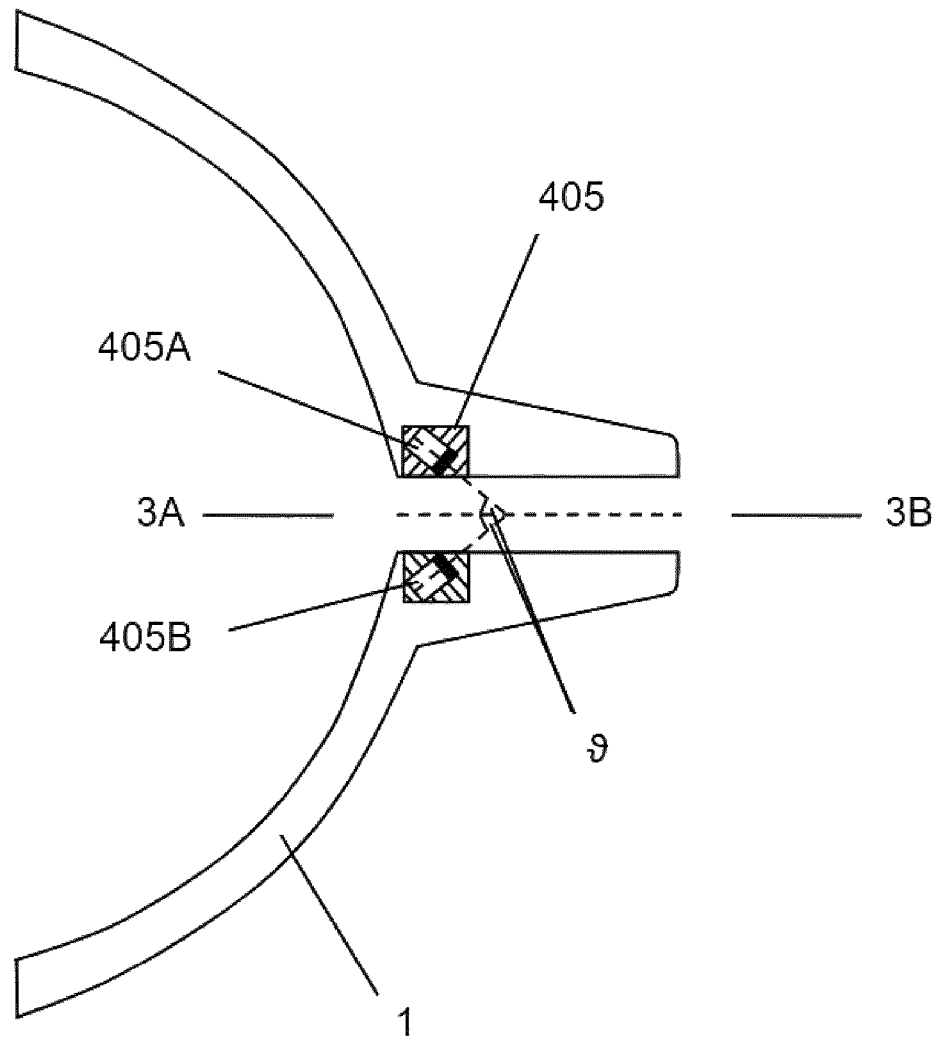
FIG. 4B is a schematic detail of the device of FIG. 1, in accordance with a further alternative embodiment of the invention using a Doppler sensor couple.

FIG. 4B shows another exemplary arrangement with the same function as that of FIG. 4A but where the sensor module (405) is constituted of a separate frequency source (405A) and a detector (405B) fixed in a stable position and oriented with a defined angle 'ϑ' respect to the flow channel on opposite sides of the milk flow.

Figure 5A:
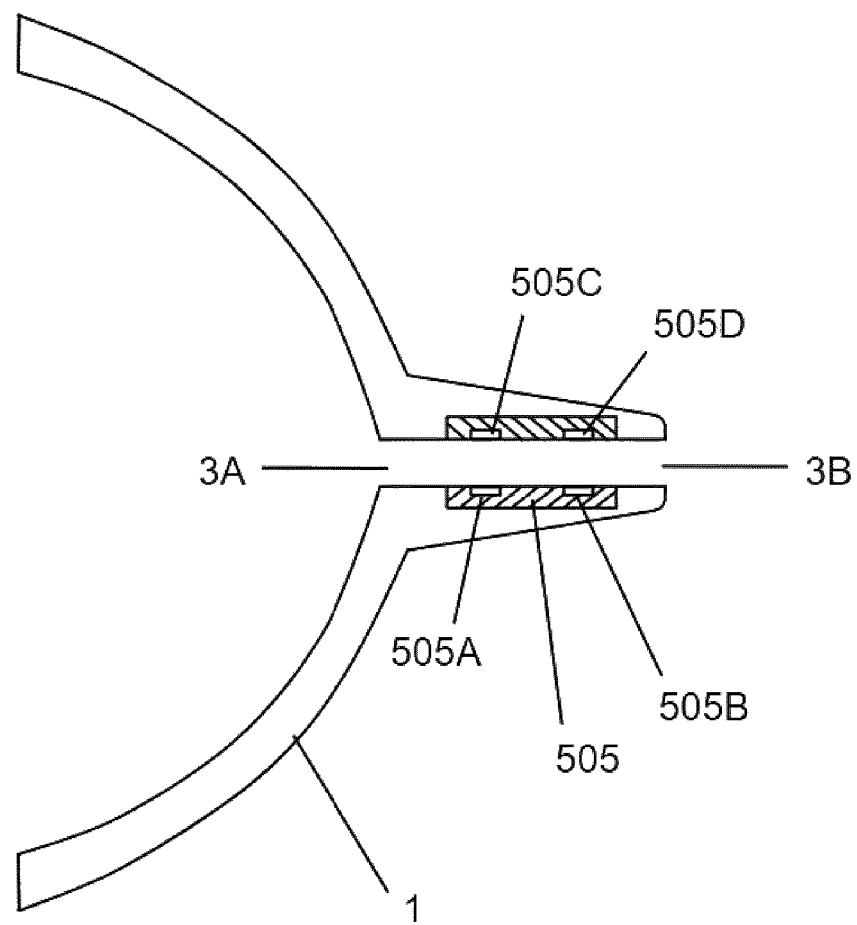
FIG. 5A is a schematic detail of the device of FIG. 1, in accordance with a further alternative embodiment of the invention using a planar time of flight optical sensor, consisting of two emitter/detector couples.

FIG. 5A shows another exemplary arrangement where the sensor module (505) is constituted of four optical active elements (505A-D). The couple of elements on the same side of the flow channel may interchangeably be two optical emitters (505A, 505B) or two optical detectors (505C, 505D). As an optical signal is transmitted by the one emitter, the optical signal received by the detector on the correspondent opposite side will be affected by the presence of particles, bubbles or other means in the fluid stream. As the same particle is detected by the other couple of elements, the time of flight difference between the two couples of elements will be measured thereby providing a flow measurement.

Figure 5B:
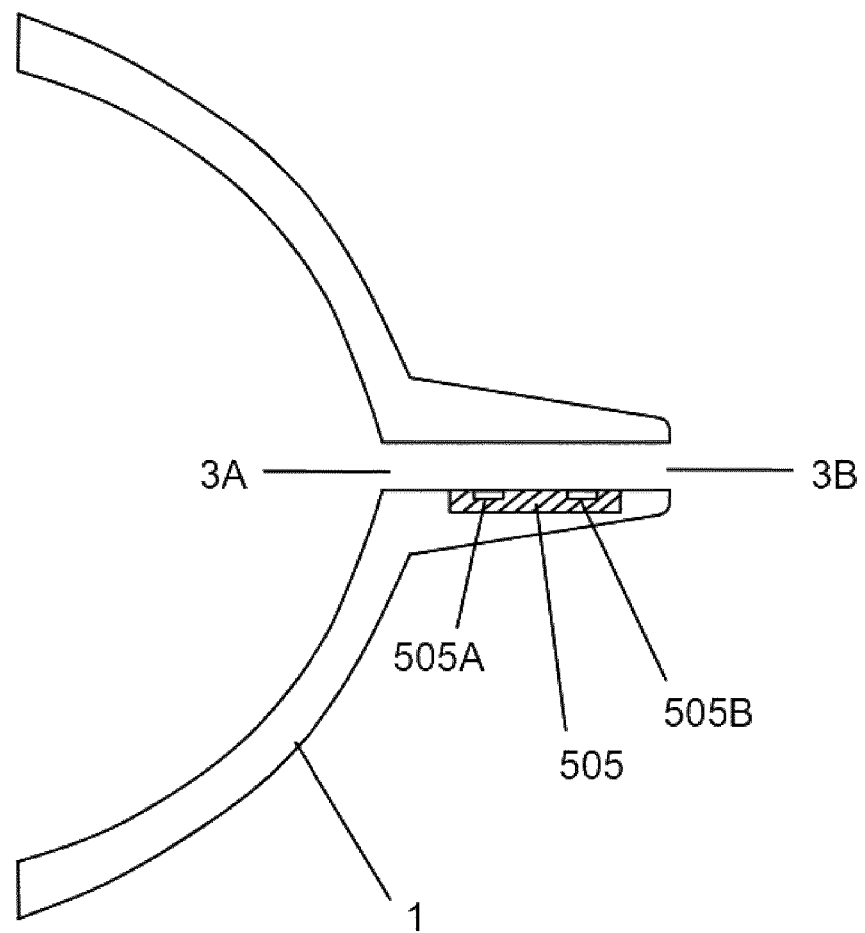
FIG. 5B is a schematic detail of the device of FIG. 5A, in accordance with a different arrangement of the sensing elements using a planar time of flight sensor, consisting of only one couple of emitter/detector.

FIG. 5B shows another exemplary arrangement alternative to the one shown in FIG. 5A where the sensor module (505) is constituted of two active elements (505A, 505B). These elements may interchangeably be one of an ultrasound emitter or an ultrasound detector. As an ultrasonic wave is transmitted by one element, its incidence at the other will be affected by the velocity of fluid in the channel thereby making possible the measurement of flow between them. The downstream/upstream sense of these may be reversed to measure the time of flight difference between the two thereby providing a flow measurement. As the path arrangement of the elements is planar, the transmission of the signal depends on reflection by the opposite wall of the channel.

Figure 5C:
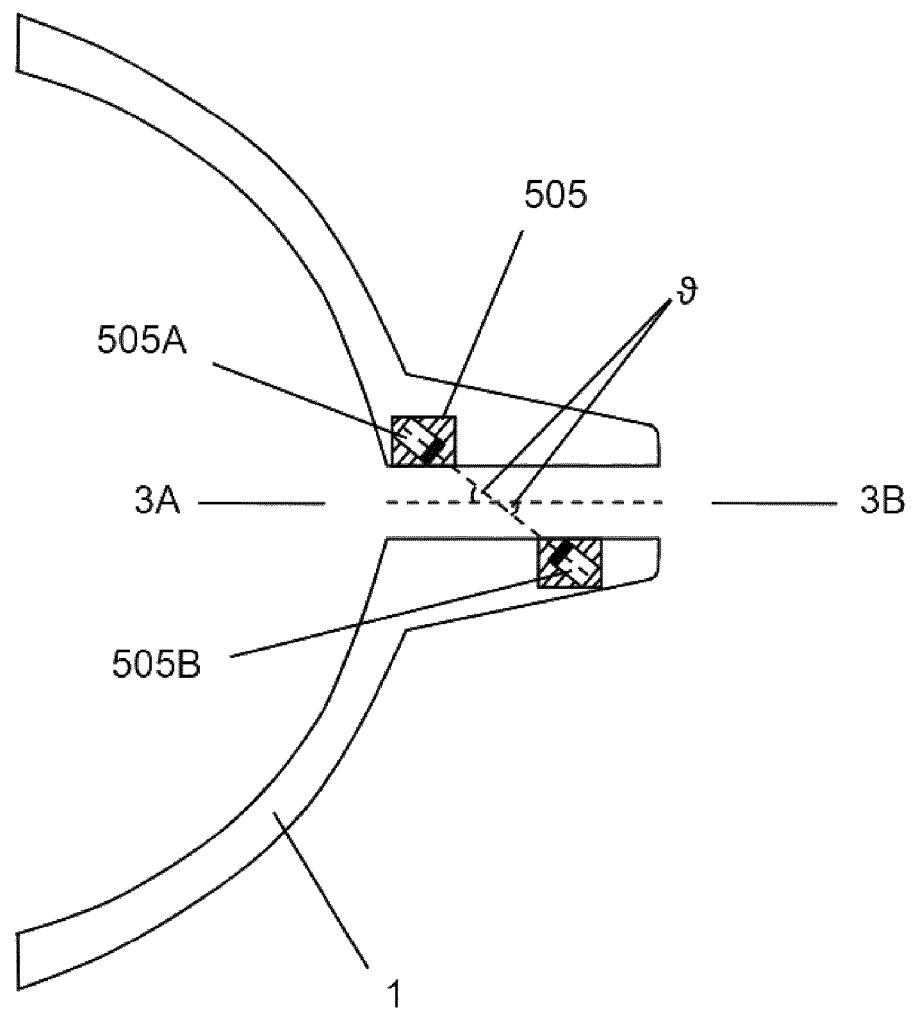
FIG. 5C is a schematic detail of the device of FIG. 5B, in accordance with a different placement of the sensing elements.

FIG. 5C shows an exemplary arrangement alternative to the one shown in FIG. 5B, where the sensor module (505) is constituted of a couple of active elements (505A, 505B) fixed in a stable position and oriented with a certain angle 'ϑ' respect to the flow channel and the milk and arranged on opposite sides of the channel. This configuration provides for a direct time of flight signal path through the fluid so does not require signal reflection.

Figure 5D:
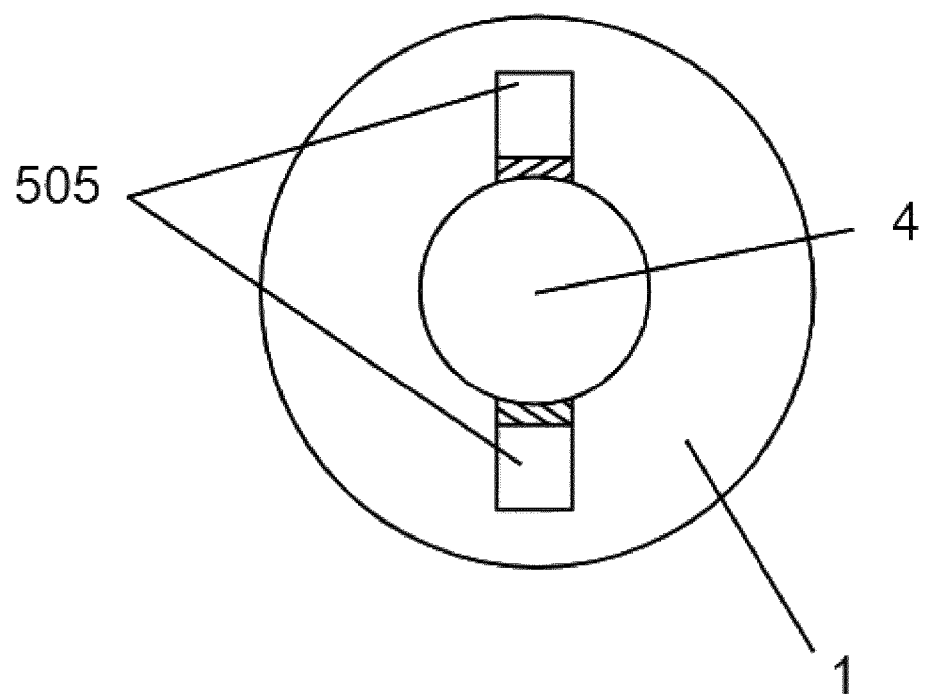
FIG. 5D is a schematic detail in frontal view of the device of FIG. 5C.

FIG. 5D shows a frontal view of the channel with the same arrangement of FIG. 5C, where a couple of active elements (505) are fixed in a diametrically opposed stable position, and oriented with a certain angle 'ϑ' respect to the flow channel (4) and the milk flow. Said sensors are integrated in the silicon rubber of the nipple shield (1).

Figure 5E:
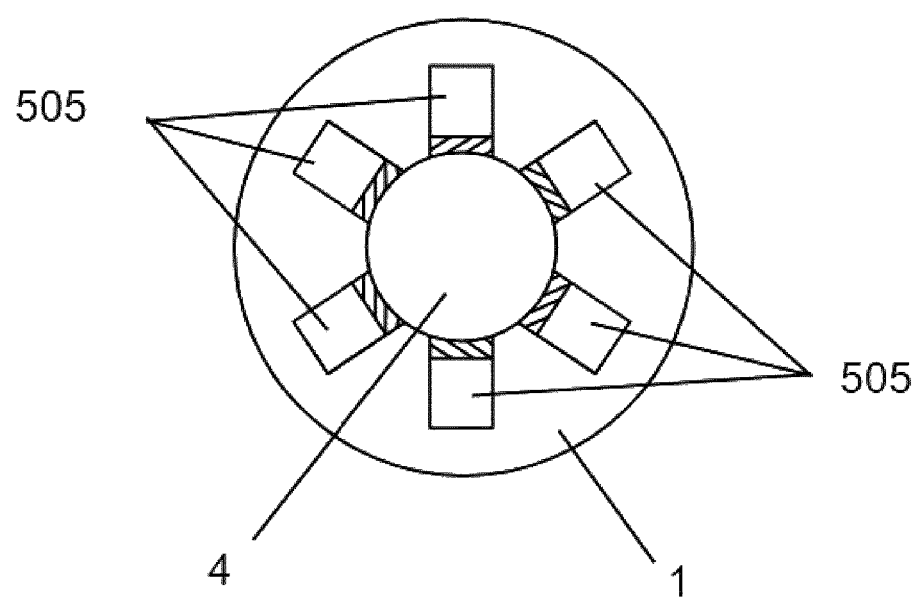
FIG. 5E is a schematic detail in frontal view of the device of FIG. 5C adapted with multiple time of flight sensor couples to implement flow tomography.

FIG. 5E shows a frontal view of the channel with the same arrangement of FIG. 5C, where more (three) couples of active elements (505) are fixed in a diametrically opposed stable positions, and oriented with a certain angle 'ϑ' respect to the flow channel (4) and the milk flow. Said sensors are integrated in the silicon rubber of the nipple shield (1) and may be used in this arrangement for flow tomography.

The introduction of sensing elements with no parts in relative motion with respect to the fluid flow will advantageously eliminate the effect of the sensor mass on the flow estimation. In fact, a thermal sensing unit will involve lightweight supports when mounted transverse to the fluid flow, while the other sensing technologies herein described will be mounted in parallel, or will be orientated with a certain angle 'ϑ' respect to the flow and in a fixed position on the sides of the flow channel, leaving the measurements unaffected by gravity.

Figure 6:
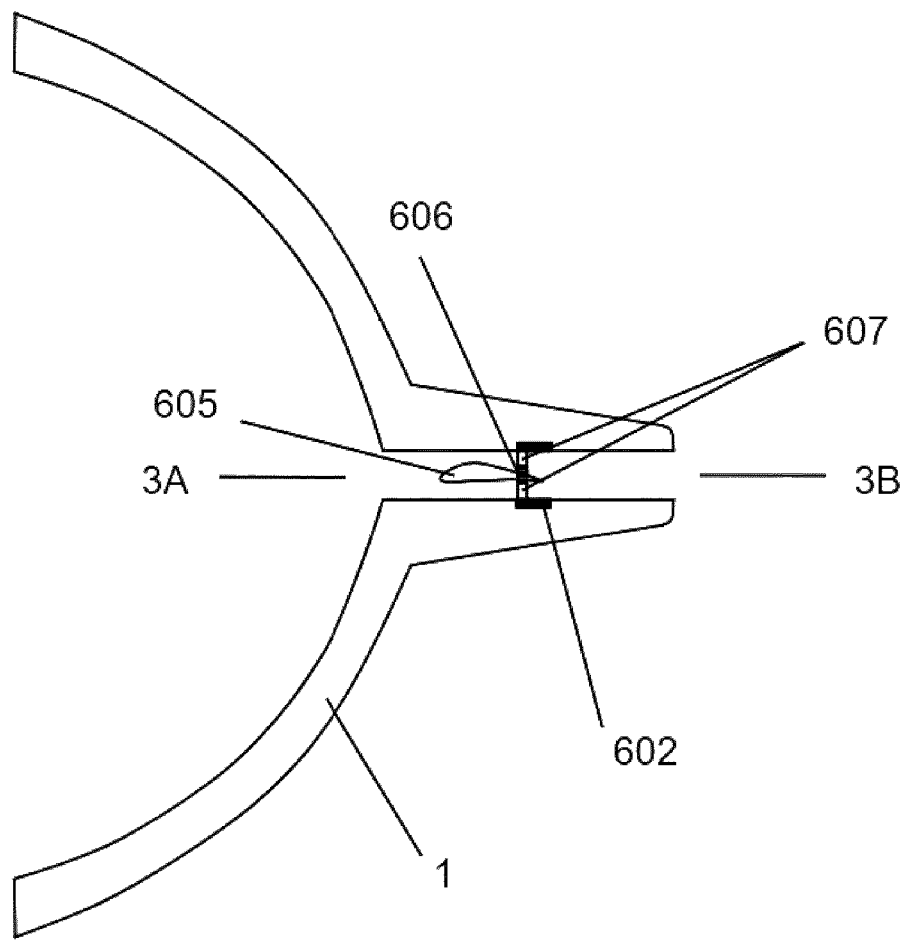
FIG. 6 is a schematic detail of the device of FIG. 1, in accordance with a further alternative embodiment of the invention using a wing or hydrofoil.

FIG. 6 shows another exemplary arrangement where the sensor module (602) is constituted of one member (605) shaped with a high camber wing profile mounted horizontally in the flow channel and respect to the direction of milk flow, and close to the input port (3A) of the flow channel. Said member is anchored to the flow channel on its trailing edge by means of a pivot (606), and is kept in position in the flow channel by means of two flexible elements (607), one acting on the upper part and one on the lower part of the member. The flow on the sensing member will cause the deflection of said flexible elements, on which strain gages are mounted, where the amount of the deflection respect to the resting condition being measured by the connected circuitry (not shown) and being an indication of the flow rate. In another arrangement, the wing-shaped member (605) can be placed vertically in the flow channel, anchored on its trailing edge by means of one flexible element on the top and one on the bottom and on which sensing gages are mounted, this vertical configuration compensating for shocks the device can undergo during operation.

Due to the sensitivity requirement to very low flow rates (upper μl/s to lower ml/s range) it is advantageous to prefer sensing components for the measurement circuitry whose characteristics will not cause perturbation to the measured signal. This optimisation of the measurement circuitry can adopt various forms, as may be apparent to the person of ordinary skill.

In all the described embodiments, it will be appreciated that additional elements may also be incorporated dependent on the desired sensitivity of the sensor module.

Referring to FIG. 1, the signals from the sensing elements may be conveyed along wires in the bonded section of the flexible material (not shown) and exited from the sensor module at a location convenient to the design of the unit. If manufacturing methods allow, all or some of the sensor components, support member, connected circuitry and flatflexible-cable may be combined into a single unit enabling the simplification of the device and its assembly. The sensor unit would be required to allow only approved food-grade materials to contact the milk flow channel. Where other materials were required these would need to be encapsulated in a food-grade material such as silicone or PTFE (for example that sold under the Teflon™ brand). Other substances for which concerns have been raised in the area of baby feeding, for example bisphenol-A, should also be excluded irrespective of their approval status.

In use, the shield will be located on the breast and the power/communication cables coupled to the processing unit (7). The operation of the sensing shield (1) and of the processing unit (7) has already been described in the previous application (PCT/EP2017/067445 of 11$^{th}$ Jul. 2017) and apply also to the present teaching.

1. The unit is powered up and the sensor settles on a baseline value within a certain warm-up time. This will be a value with no fluid present in the channel which will be expected to be different to the zero-flow value with milk present due to temperature, convection, etc. For the purposes of explanation, this value could hypothetically be attributed a value of 100.

2. The feeding session starts and the first and subsequent pulses increase as a result of the sensed milk flow within the channel. The output values would increase relative to the zero value above, for example to a value of 1000. It will be appreciated that the output of the sensor will be a series of pulsed values responsive to the induced milk flow resultant from the suckling child. Between each maximum pulse value, the values sensed do not fully settle back to the initial value though due to the time-constant of the sensor or residual flow between the pulses. The peak-to-peak value for these pulses is assumed therefore to be 900 and a corresponding volume is displayed.

3. It is characteristic of a feeding session that relatively long periods have no milk expression. When the first of these is encountered the output settles back to a steady value of 200 indicating the zero-flow value with milk present. It is now clear that the value for the initial pulses peaked at 800 instead of 900, so the volume may be re-calculated based on algorithmic computations effected within the processing unit 7.

4. It will be appreciated that displaying the re-calculated value instantaneously may result in the displayed volume reducing which would seem erroneous and could cause concern. As a result, the unit (7) may delay providing a visual indication of the first measurement value until additional data is processed. Other arrangements would include providing an indication of increase in accuracy over time or a measurement lock type symbol on the display so as to provide the user with visibility as to the accuracy being provided.

It will be appreciated from the above that the present teaching provides a breastfeeding milk flow measurement device that senses milk flow based on changes in electrical characteristics of a flow sensor that is provided within a flow channel of the flexible nipple shield. The device provides a comparison between the sensed electrical characteristics of the sensor and calibration data to provide an estimate of the milk flow through the channel- and hence the volume of milk that passes to the feeding child in any feeding session. In the preferred configuration, the sensed electrical characteristics are dependent on thermal properties of the sensor— the sensor operably being responsive to a cooling effect resultant from a passing of milk passed the sensor.

Given the electronic component and mechanical tolerances of the component parts of the device, there will be part-to-part variation in the flow response of the sensor and to ensure accuracy of measurement a calibration protocol is required. In a preferred implementation, this protocol is one that is conducted as part of the production process. It will be appreciated that the flexible nipple shield includes electrical components that are provided within a completely moulded or sealed arrangement within the flexible elastomer that defines the material of the shield. To provide calibration of these components it is necessary to interface with them without actually using of physical connections in loading calibration values. It is also undesirable from a process point of view to customise each firmware image to be loaded to the device to the calibrated values.

To address these problems, the present teaching provides a calibration routine which is based on providing a complete electronics assembly including the sensor. This is typically in the form of a printed circuit board, PCB, with an associated microcontroller, MCU, chip. At this stage in the process there are no enclosures or moulds assembled over the PCB with the MCU chip. A generic firmware image is loaded through an electronics test harness with physical (pin) connections. This image contains all functionality including Bluetooth wireless operation and the Bluetooth service is programmed to contain empty "characteristics" (Bluetooth variables) for calibration values. The electronics assembly is then inserted in to the device case and moulds and the device is manufactured to completion. The completed device is clamped into a calibration harness which allows known flow patterns to be realised in the device flow channel. The range of flow pattern to be realised will include small variations of fluid volume within the breastfeeding flow rate range (0.007-2.8 ml/s), and will be performed over a time frame in the order of minutes. The responses to the flow patterns are converted into calibration coefficients by a computer attached to the calibration harness, and these coefficients are loaded over-the-air (OTA) to the device via a Bluetooth interface attached to the computer. The values are then made read-only by a subsequent Bluetooth command. Using this sequence only a generic firmware image is used and no physical connection to the device is required for the purpose of calibration.

It will be understood that the heretofore described nipple-shield mounted sensor with associated electronic interface and interconnect advantageously allows for measurement and display of milk flow and volume during breastfeeding. The sensor is mounted in the tip of the nipple-shield in order to minimise intrusion between mother and child. The dimensions of the sensor and associated cabling are such that the device does not appear substantially different to a nipple-shield alone, thereby having minimal impact on the feeding session. Microlitre flow levels are measured directly by the sensor in order to relay accurate, real-time information on milk volume back to the feeding mother. The electronics unit amplifies the sensor input and digitally processes the data with software algorithms to determine the fluid volume. It will be appreciated that the examples of such a measurement device that provides real time measurement values indicative of a milk flow from a mother to her baby are provided to assist in an understanding of the present teaching.

As mentioned above, the sensor module of the present teaching is desirably integrally formed in an elastomeric nipple shield. The integration of the sensor module associated processing components and a connection cable, such as the flat flexible cable described above in the nipple shield can be effected using injection moulding techniques. A particularly advantageous mechanism is one that is effected using two-shot injection moulding. Said manufacturing method will ensure an advantageous placing of the components into the flexible nipple shield.

Figure 11A:
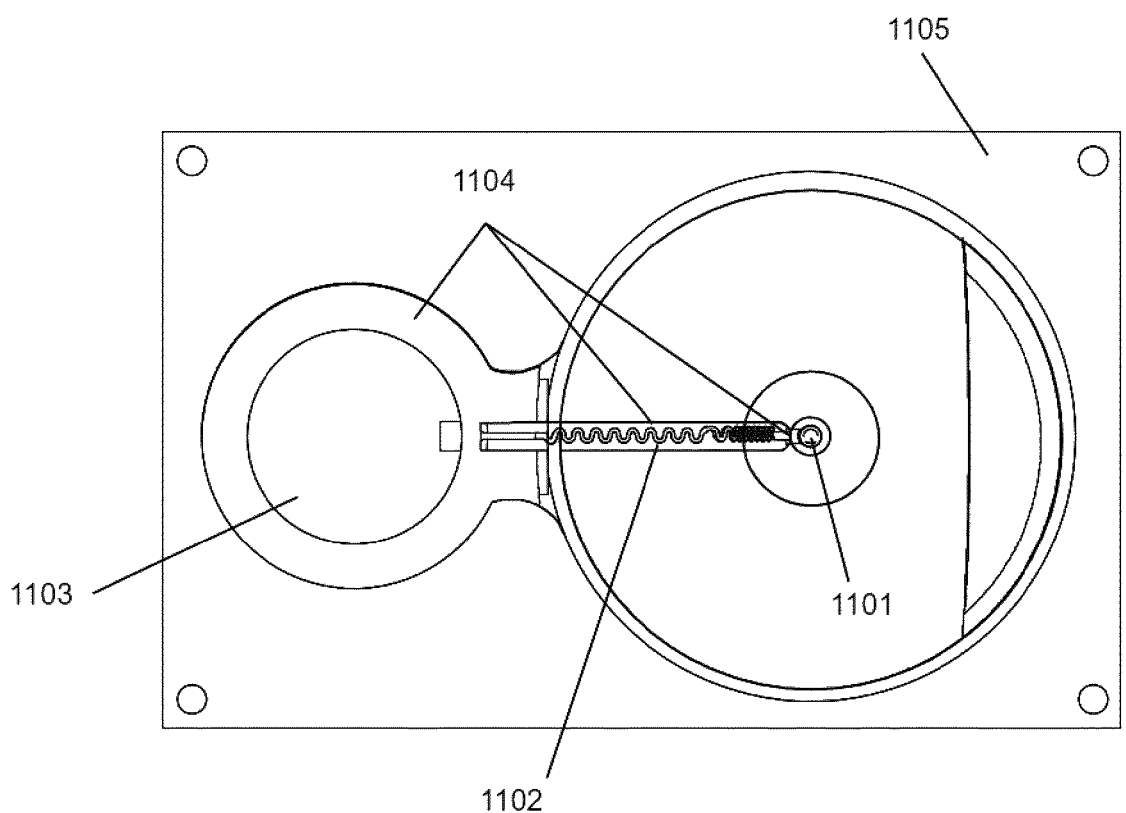
FIG. 11A is a schematic representation, in front view, of the first part of the mould used to fabricate a device in accordance with the present teaching.
Figure 11B:
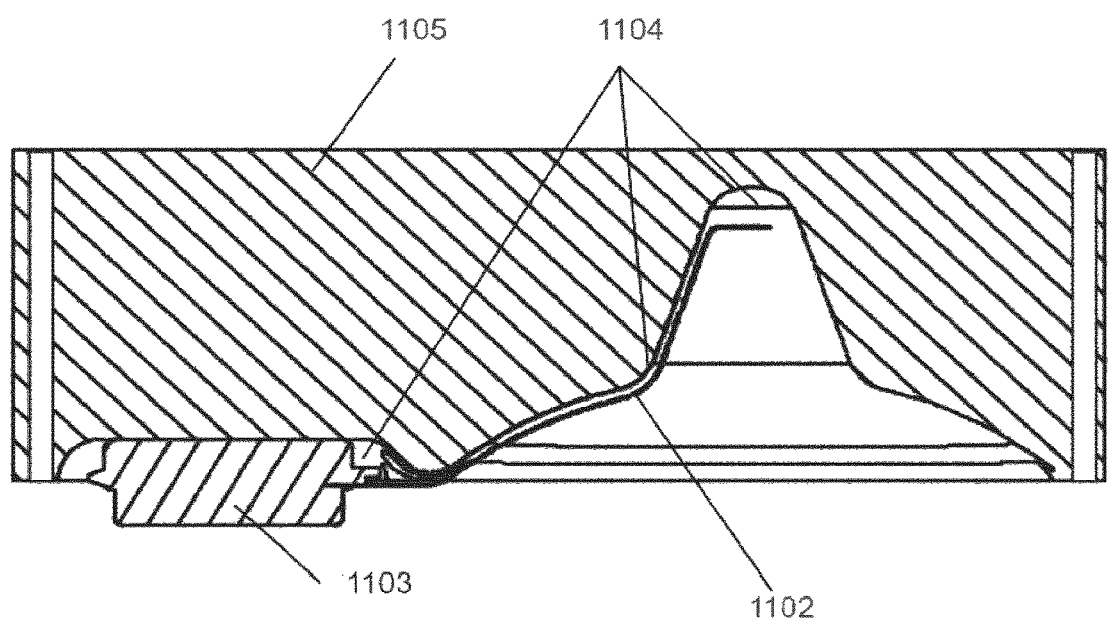
FIG. 11B is a schematic representation, in side view, of the first part of the mould used to fabricate a device in accordance with the present teaching.

FIGS. 11A and 11B show respectively a front and side view of the first part of the mould used during the manufacturing process in order to fabricate the integrated breastfeeding device. The proposed manufacturing method consists of an injection moulding process, the number of injection moulding steps starting from two and depending on the typology of the components to be integrated in the shield. For the first step of the moulding, the sensor module (1101), the flat flexible cable (1102) and the processing unit (1103) will be placed in a dedicated housing (1104) of the mould (1105), the shape and dimensions of the housing allowing to keep in place said components by clamping (or other fastening methods).

The dedicated housing (1104) will allow to shape the flat flexible cable into its final configuration within the shield, the flexible substrate of the cable allowing to easily bend it into the mould without pre-stretching. The dimensions of the housing can be designed to fit precisely the geometry of the components, or to leave a certain tolerance (i.e. free space) around them. In certain circumstances, the housing for the flat flexible cable will be required to leave tolerances in the order of μm allowing some degrees of freedom to the cable within the polymeric material of the shield, and avoiding its detachment during the device's operation and handling.

During the manufacturing process, in order to integrate all the components into the shield, the single components may be assembled together to facilitate their collocation into the mould, or they can be placed individually in the mould by means of clamping (or other fastening methods).

To facilitate the collocation of the active components into the shield, an assembly of two or all of them, or the individual components, can be encapsulated into a polymeric material, which can be (but not limited to) the same of the shield. Said encapsulated individual elements (or assembly) can be then integrated within the polymeric shield during the first step of the injection moulding process by means of clamping (or other fastening methods).

Figure 12A:
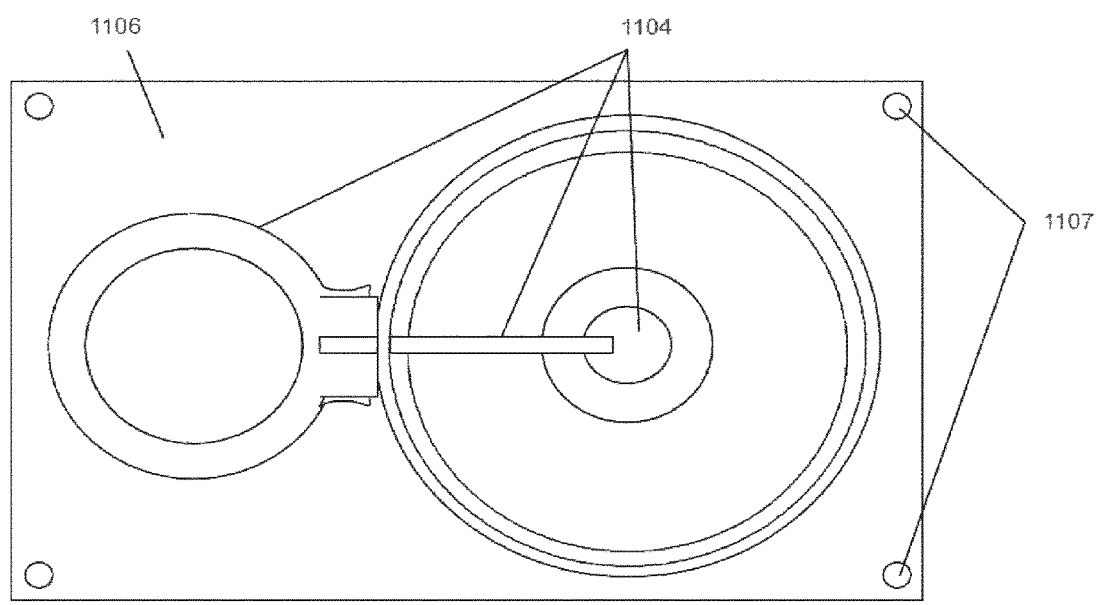
FIG. 12A is a schematic representation, in front view, of the second part of the mould used to fabricate a device in accordance with the present teaching.
Figure 12B:
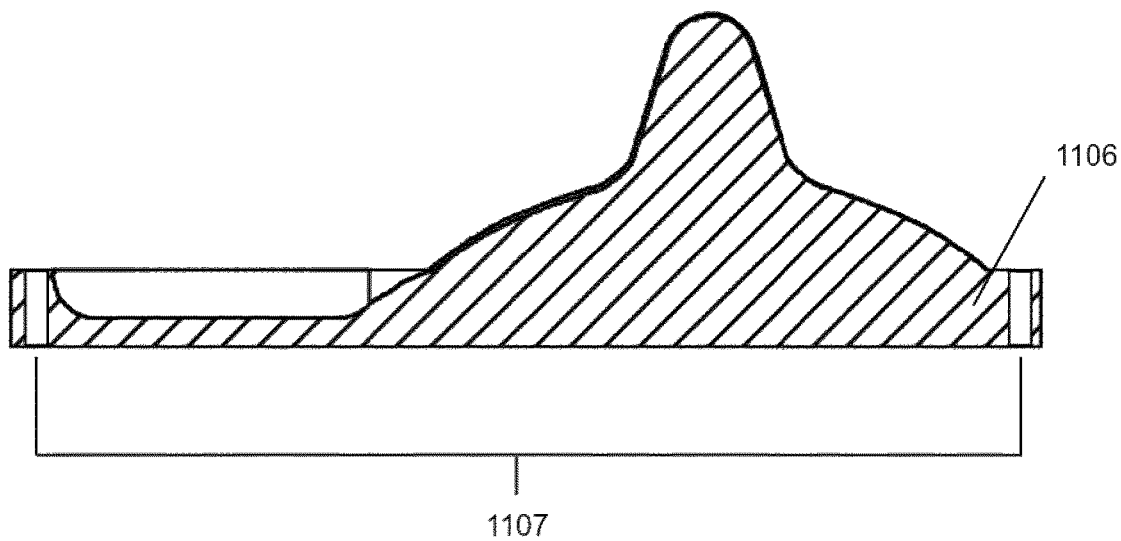
FIG. 12B is a schematic representation, in side view, of the second part of the mould used to fabricate a device in accordance with the present teaching.

FIGS. 12A and 12B show respectively a front and side view of the second part of the mould used during the manufacturing process in order to fabricate the integrated breastfeeding device. Once the components (1101-1103 in FIG. 11A-B) are placed in the first part of the mould (1105 in FIG. 11A-B), the second part of the mould (1106) is placed over the first part (1105 in FIG. 11A-B). A dedicated housing (1102) will enclose the components (1101-1103 in FIG. 11A-B), while holes (1107) coincident with those on the other side of the mould will be used to close the two parts using screws (or other fastening methods).

Figure 13A:
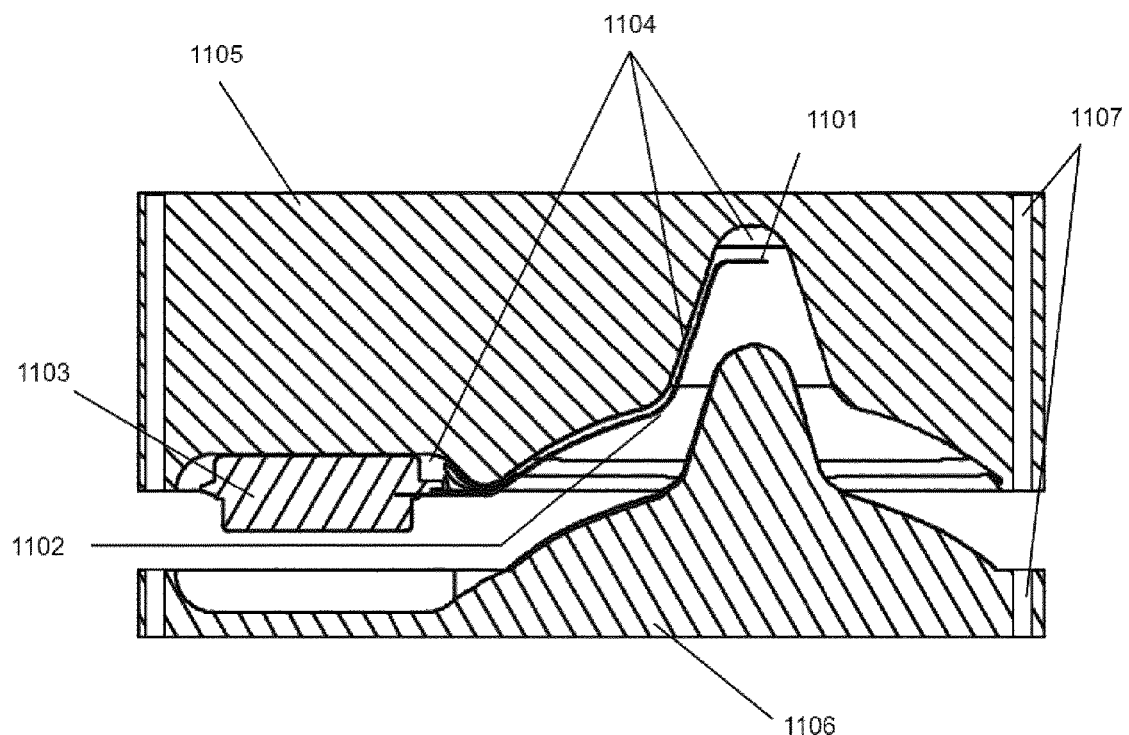
FIG. 13A is a schematic representation, in side view, of the last step of the injection moulding process for the fabrication of a device in accordance with the present teaching, when the incomplete shield with the integrated components is closed within a mould.

With reference to FIG. 13A, once the components (1101-1103) are clamped in the dedicated housing (1104), both the first (1105) and the second (1106) parts of the mould are closed together via the holes (1107), and a first shot of polymeric material is injected into the mould. The polymer then undergoes a first processing step, in which time and temperature/humidity/pressure conditions are dictated by the selected rubber.

Once cured, the first mould is opened and the polymeric shield/measurement unit assembly is detached from the mould used for the first injection step and is placed in another mould to undergo another injection step. The second injection step, when in some circumstances is the last step, will ensure the complete encapsulation of the components left uncovered by the polymer on the side they had in contact with the mould during the previous injection steps. The second mould, which parts are similar to those already described (1105, 1106), will conform (or will leave some degree of tolerance) to the shape of the assembly obtained with the previous injection steps.

Figure 13B:
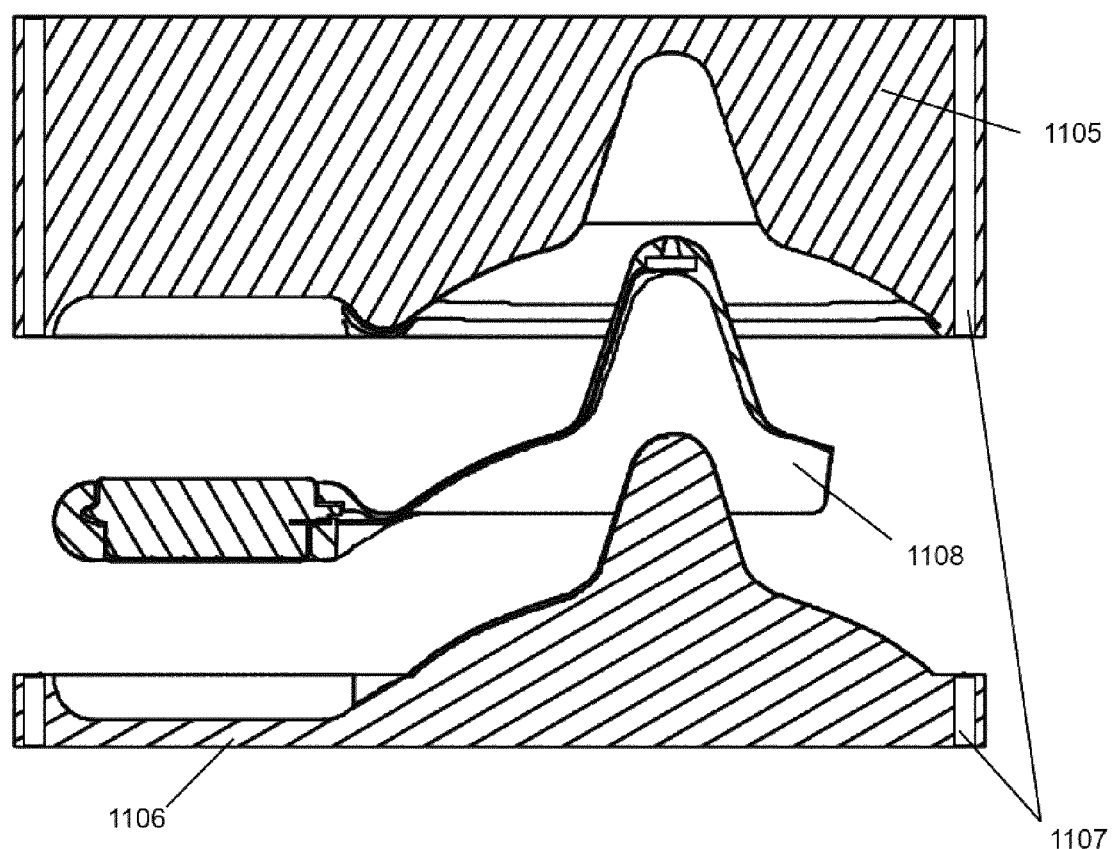
FIG. 13B is a schematic representation, in side view, of a device in accordance with the present teaching, when extracted from the mould after the last injection step.

With reference to FIG. 13B, once the assembled shield is placed in the mould by means of clamping (or other fastening methods), the mould is closed using screws passed through the holes (1107) of the mould (or other fastening methods), and a further injection of the same polymer used for the previous shots, or other materials, is performed. The polymer is then cured with the appropriate curing time and temperature/humidity/pressure conditions. Once the material is cured, the mould is opened in its two parts (1105, 1106) and the integrated shield (1108) is ready for use.

In some circumstances, the fabrication of a hollow channel for the insertion of the flat flexible cable can be required. In this case, the housing in the first mould dedicated to receive the flexible cable will be replaced by a filled channel, which shape and dimensions will correspond to those of the wire, with a certain tolerance (in the order of μm). Said negative mould of the channel for the cable will allow for the creation of a hollow channel after the polymer curing. The shape of the hollow channel can resemble that of the flat flexible cable, or can be just straight and cylindrical.

Accordingly with another solution for the development of the electrical connections between the flow sensor and the processing unit, the above mentioned hollow channel can be filled with low-noise conductive inks by means of an additional injecting step.

While specifics have been described, it will be appreciated that modifications can be made without departing from the scope of the invention.

The words comprises/comprising when used in this specification are to specify the presence of stated features, integers, steps or components but does not preclude the presence or addition of one or more other features, integers, steps, components or groups thereof.

The invention claimed is:

1. A breastfeeding milk flow measurement device comprising:
   a flexible nipple shield adapted to operably conform in shape with a nipple, the shield defining a flow-channel through which a volume of milk will operably pass from the nipple to a feeding baby,
   the device further comprising a sensor module having a flow sensor provided within the nipple shield, the flow sensor comprising first and second active elements mounted on supporting substrates located between an input port and an output port of the flow-channel, and being provided perpendicular to the flow and within the flow-channel,
   wherein the supporting substrates are located within the flow channel at a level of a flow channel cross-section by a common supporting ring provided within the nipple shield,
   wherein the first active element of the flow sensor comprises a heatable temperature dependent resistor which is located within a mid-portion of the flow-channel, wherein the resistor is operably heated to, and maintained at, a first temperature $T_1$, greater than an ambient temperature, $T_2$, of milk flowing in the flow channel,
   the second active element of the flow sensor comprising a resistor, placed close to the resistor of the first active element and being configured to measure the temperature variation of the milk with respect to the temperature of the first active element by detecting a variation of its resistance, the flow of the milk causing a measurable cooling effect on the resistor of the first active element, the device being configured to use the measurable cooling effect to generate an output signal indicative of the milk flow within the channel.

2. The device of claim 1 wherein the flow sensor is a non-mechanical sensor, comprising no parts which move relative to the milk flow.

3. The device of claim 1 where the resistor of the first active element is operably heated by its own electrical connection or is coupled to a secondary heat source to raise its temperature above the ambient temperature of the milk.

4. The device of claim 1 comprising an anemometry circuit, the anemometry circuit being coupled to the resistors and arranged to monitor electrical characteristics of the resistors and to use changes in those monitored electrical characteristics to generate the output signal.

5. The device of claim 4 wherein the anemometry circuit is selected from one of a constant temperature anemometry (CTA) circuit, a constant current anemometry (CCA) circuit, or a constant voltage anemometry (CVA) circuit.

6. The device of claim 1 where resistor is coupled to a power-supply, power to the resistor being operably continuously provided through an analog bridge circuit or pulsed through a digital modulation scheme such as pulse width modulation (PWM) or sigma-delta ($\Sigma\Delta$) modulation.

7. The device of claim 1 where the resistor is a thin-wire, thin-film, RTD, thermistor, bulk silicon device, junction silicon device or any other resistive component with a measurable temperature coefficient of resistance.

8. The device of claim 1, where the sensor module comprises a plurality of sensing elements arranged in an array along the flow channel.

9. The device of claim 1 comprising a memory element for storing calibration coefficients of the flow sensor.

10. The device of claim 1 comprising a memory element for storing historical feeding data.

11. The device of claim 1 comprising a memory element for storing sensor wear and/or use information.

12. The device of claim 1 comprising a cable extending from the nipple shield and wherein the memory element is located on or embedded in the cable.

13. The device of claim 1 comprising a cable extending from the nipple shield and connected to a processing unit.

14. The device of claim 1 comprising a transmitter.

15. The device of claim 14 wherein the transmitter uses wireless communication protocols to communicate with a remote device.

16. A measurement system comprising:
a processing unit;
a visual display; and,
a breastfeeding milk flow measurement device, the breastfeeding milk flow device comprising a flexible nipple shield adapted to operably conform in shape with a nipple, the shield defining a flow-channel through which a volume of milk will operably pass from the nipple to a feeding baby, the device further comprising a sensor module having a flow sensor provided within the nipple shield, the flow sensor comprising first and second active elements mounted on supporting substrates located between an input port and an output port of the flow-channel, and being provided perpendicular to the flow and within the flow-channel, wherein the supporting substrates are located within the flow channel at a level of a flow channel cross-section by a common supporting ring provided within the nipple shield, wherein the first active element of the flow sensor comprises a heatable temperature dependent resistor which is located within a mid-portion of the flow channel, wherein the resistor is operably heated, and maintained at a first temperature, $T_1$, greater than an ambient temperature, $T_2$, of milk flowing in the flow-channel, the second active element of the flow sensor comprising a resistor, placed close to the resistor of the first active element and being configured to measure the temperature variation of the milk with respect to the temperature of the first active element by detecting a variation of its resistance, the flow of the milk causing a measurable cooling effect on the resistor of the first active element, the device being configured to use the measurable cooling effect to generate an output signal indicative of the milk flow within the channel,
wherein the processing unit is configured to receive flow sensor data from the device and provide, in the visual display, a visual indication of the flow measured.

17. The system of claim 16 comprising a data-logger configured to collate received flow sensor data with at least one of personal information, time-of-day, or medical notes.

18. The system of claim 16 wherein the processing unit is integrated into a wrist unit to be worn during feeding.

19. The system of claim 16 configured to provide storage of historical feeding records for subsequent retrieval and display in a numeric or graphical fashion.

20. The system of claim 16 configured to allow individual election of a measurement from one of a left or right breast to facilitate independent tracking of milk flow from each breast independently.

21. The system of claim 16 wherein the visual display provides a graphical representation of pulsations of milk flow such as in the form of a bar-graph, a dial, or the appropriate percentage of the display becoming inverse in response to a dynamic reading.

22. The system of claim 16 wherein the processing unit is configured to provide real-time accuracy bounds of a given measurement in a numeric or graphical fashion, the real-time accuracy bounds being displayed on the visual display.

23. The system of claim 16 configured to track usage of the device and provide an indication of when actual usage approaches pre-calibrated expected usage.

24. The system of claim 16 wherein the processing unit is a smartphone, the visual display being a screen of the smartphone, the smartphone having executing thereon application software that receives and processes flow sensor data from the sensor and provides, in the visual display, a visual indication of the flow measured.

* * * * *